United States Patent
Teirstein et al.

(10) Patent No.: US 8,523,824 B2
(45) Date of Patent: Sep. 3, 2013

(54) GUIDEWIRE AND CATHETER MANAGEMENT DEVICE

(75) Inventors: Paul S. Teirstein, La Jolla, CA (US); William Atkinson, Escondido, CA (US); William Gould, Fallbrook, CA (US); Yem Chin, Burlington, MA (US); Paul Scopton, Winchester, MA (US); Robert F. Carmichael, Jr., Needham, MA (US)

(73) Assignee: Vascular Solutions, Inc., Minneapolis, MN (US)

( * ) Notice: Subject to any disclaimer, the term of this patent is extended or adjusted under 35 U.S.C. 154(b) by 300 days.

(21) Appl. No.: 12/498,985

(22) Filed: Jul. 7, 2009

(65) Prior Publication Data

US 2010/0010475 A1  Jan. 14, 2010

Related U.S. Application Data

(63) Continuation-in-part of application No. 12/217,852, filed on Jul. 8, 2008, now abandoned.

(51) Int. Cl.
*A61M 5/32* (2006.01)

(52) U.S. Cl.
USPC ............................................. 604/174

(58) Field of Classification Search
USPC .............. 604/174, 177–180; 606/148–150; 206/370
See application file for complete search history.

(56) References Cited

U.S. PATENT DOCUMENTS

| | | |
|---|---|---|
| 2,727,512 A | 12/1955 | Muller |
| 3,491,971 A | 1/1970 | Fisher |
| 3,630,195 A | 12/1971 | Santomieri |
| 3,696,920 A | 10/1972 | Lahay |
| 4,185,636 A | 1/1980 | Gabbay et al. |
| 4,336,806 A | 6/1982 | Eldridge, Jr. |
| 4,492,229 A | 1/1985 | Grunwald |
| 4,609,171 A | 9/1986 | Matsui |
| 4,820,274 A | 4/1989 | Choksi et al. |
| 4,896,465 A | 1/1990 | Rhodes et al. |
| 4,907,332 A | 3/1990 | Christian et al. |
| 4,971,271 A | 11/1990 | Sularz |
| 5,202,538 A | 4/1993 | Skirpan |
| 5,224,674 A | 7/1993 | Simons |

(Continued)

FOREIGN PATENT DOCUMENTS

| | | |
|---|---|---|
| DE | 1272412 B | 7/1968 |
| EP | 0116826 A1 | 8/1984 |
| EP | 0720836 A2 | 7/1996 |
| WO | 2005051472 A2 | 6/2005 |

*Primary Examiner* — Kami A Bosworth
(74) *Attorney, Agent, or Firm* — Schwegman Lundberg & Woessner P.A.

(57) ABSTRACT

Provided are devices and methods for catheter and guidewire management in a surgical setting. In one implementation, the device includes a housing having a curved bottom surface for accommodating the shape of a patient's leg. A retaining member is included, which can retain one or more guidewires, catheters, or the like. In another embodiment, the housing may include a number of vertical supports between which are mounted at least one retaining member housing. The retaining member housing may in turn house a retaining member, suitable for receiving and retaining one or more elongated devices such as catheters or guidewires. The retaining member may have a suitable size, shape, and level of flexibility to allow a catheter or guidewire to be placed therein and held with a desired level of force until such a time as a user desires to remove the catheter or guidewire.

22 Claims, 25 Drawing Sheets

(56) References Cited

U.S. PATENT DOCUMENTS

| | | |
|---|---|---|
| 5,226,892 A | 7/1993 | Boswell |
| 5,363,539 A | 11/1994 | Tisol |
| 5,389,082 A | 2/1995 | Baugues et al. |
| 5,735,821 A | 4/1998 | Dobkin |
| 5,743,497 A | 4/1998 | Michael |
| 5,795,335 A * | 8/1998 | Zinreich .............. 604/174 |
| 5,830,157 A | 11/1998 | Foote |
| 6,458,104 B2 | 10/2002 | Gautsche |
| 6,554,808 B1 | 4/2003 | Cook |
| 6,616,107 B1 | 9/2003 | Hargreaves |
| 6,647,991 B2 | 11/2003 | Silva |
| 6,688,679 B2 | 2/2004 | Droulez |
| 6,872,192 B2 | 3/2005 | Nash et al. |
| 6,969,498 B1 | 11/2005 | Riley |
| 7,303,568 B2 | 12/2007 | Jannot |
| 7,438,265 B2 | 10/2008 | Urzua |
| 7,457,506 B1 | 11/2008 | Osborne, II |
| 7,817,444 B2 | 10/2010 | Dennes |
| 8,366,638 B2 | 2/2013 | Teirstein |
| 2002/0177789 A1 | 11/2002 | Ferry |
| 2005/0182368 A1 | 8/2005 | Gillis et al. |
| 2006/0149292 A1 | 7/2006 | Knudtson et al. |
| 2006/0237597 A1 | 10/2006 | D'Andria |
| 2006/0253048 A1 | 11/2006 | Jones et al. |
| 2007/0118079 A1 | 5/2007 | Moberg et al. |
| 2008/0076989 A1 | 3/2008 | Hete et al. |
| 2008/0097334 A1 | 4/2008 | Dikeman et al. |
| 2010/0274158 A1 | 10/2010 | Teirstein |

* cited by examiner

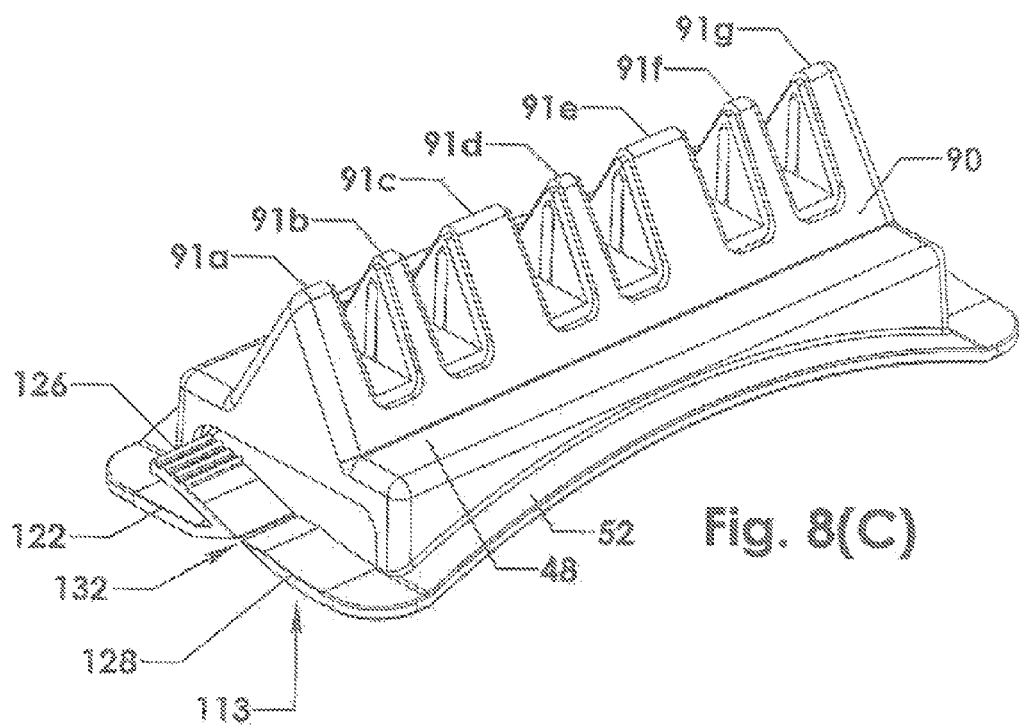
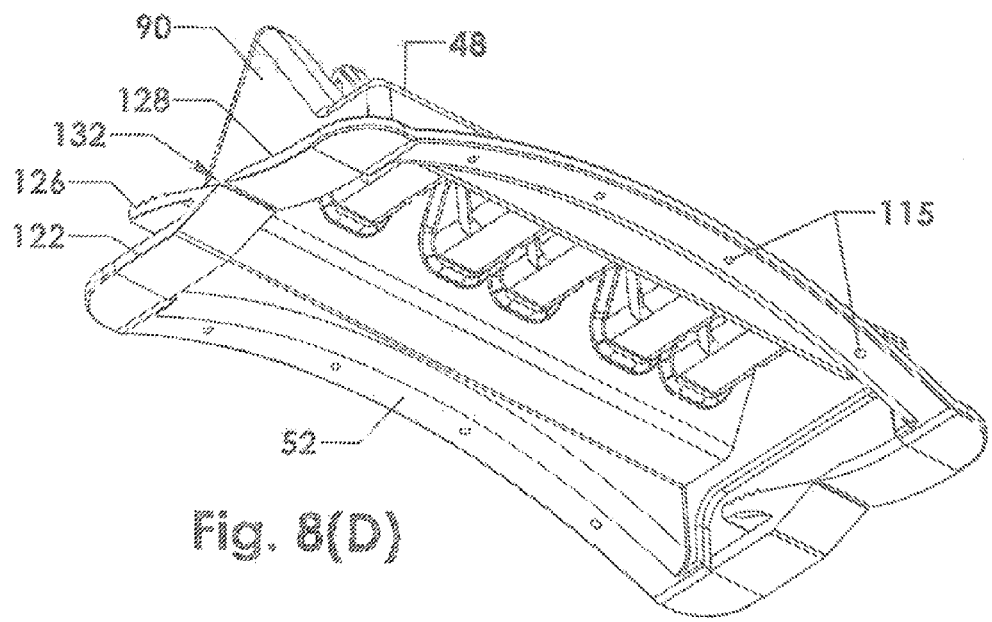

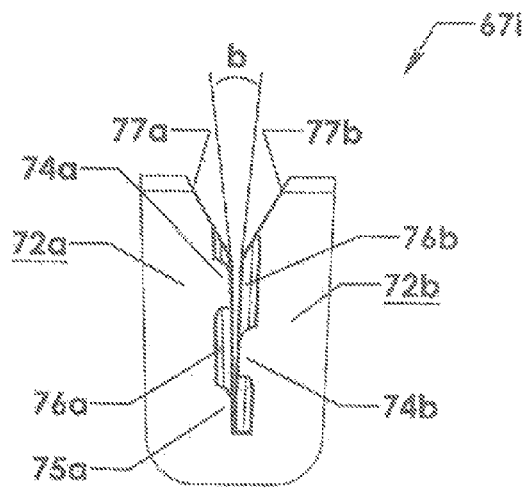
Fig. 8(E)
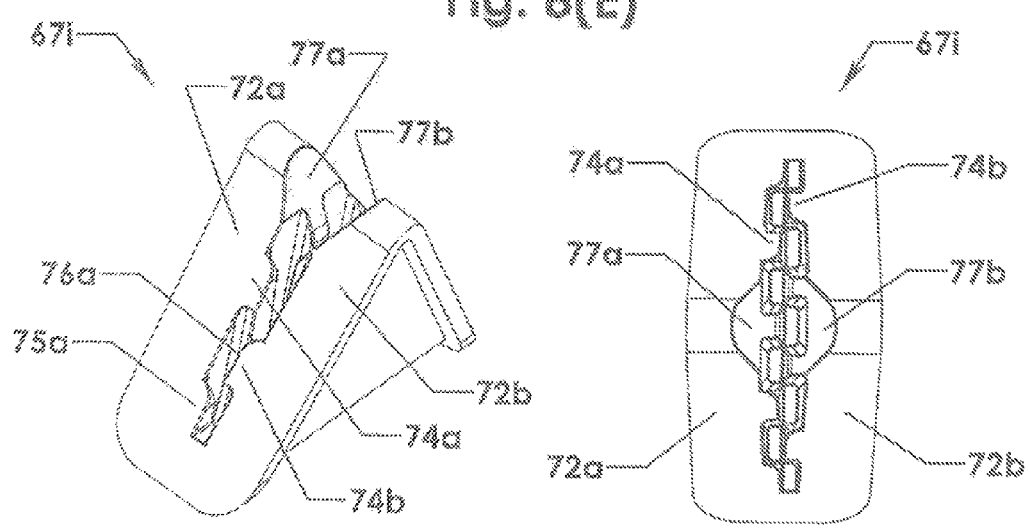
Fig. 8(F)
Fig 8(G)

GUIDEWIRE AND CATHETER MANAGEMENT DEVICE

CROSS REFERENCE TO RELATED APPLICATIONS

This application is a continuation-in-part of U.S. patent application Ser. No. 12/217,852, filed Jul. 8, 2008, entitled "Guide Wire and Catheter Management Device", the entirety of which is incorporated by reference herein.

STATEMENT REGARDING FEDERALLY SPONSORED RESEARCH OR DEVELOPMENT

Not Applicable

BACKGROUND OF THE INVENTION

1. Field of the Invention

This invention is in the field of equipment used for intravascular medical procedures, specifically flexible elongated members such as guidewires and catheters that are introduced into a patient's blood vessel.

2. Background Art

Invasive vascular procedures like balloon angioplasty and stent implantation require insertion of a guide catheter into the vasculature, usually in the femoral (leg) artery and directing the catheter to the vasculature in need of treatment, such as the heart. Through this catheter, a thin (for example 0.014 inch) wire called a guidewire, is introduced and threaded down the artery to be treated. An additional catheter or other flexible elongated member can be introduced over, or alongside, the guidewire.

The catheter prior art is replete is variations. For example, rapid exchange catheters are also used, where a guidewire enters a lumen in the distal tip of the catheter and then exits anywhere from about 1 cm to 40 cm from the distal tip, running alongside the catheter but outside of the same. In "over-the-wire" catheters, the guidewire runs inside the catheter throughout its length.

At times, the operator must treat or protect more than one vessel using the same guide catheter. In this circumstance, the operator passes two or more pairs of flexible elongated members through the same Y adaptor. The multiple flexible elongated members travel down the same guide catheter and then enter the vessel requiring treatment, with each guidewire and its associated catheter usually entering a different vessel or branch vessel in need of treatment.

The multiple guidewires and their respective catheters enter the guide catheter through the sealable entry site of the Y adaptor. Since the guidewire/catheter pairs have the same point of entry at the Y adaptor, the operator must take steps to keep the wire/catheter pairs separate from each other, and to keep each guidewire identified with the correct catheter. It is important to keep the wire/catheter pairs separate for several reasons. If the wire/catheter pairs become twisted, they will interact with one another; for instance, when the operator moves one wire or catheter, another wire or catheter may also move. Further, different devices, such as stents, are typically passed over the guidewires on the catheters; therefore, if the wire/catheter pairs become twisted with each other, accurate advancement of the associated devices is hindered. Also, since different devices are passed over the different wires on the catheters, the operator must take steps to identify each wire so as not to confuse which wire is going down which vessel or branch vessel.

Currently, the prevalent method of separating wire/catheter pairs is to use layers of sterile towels. However, towels are bulky and difficult to control. Towels securing guidewires also lie on the operative field and if the Y adaptor is moved, the towels tend to stay in place, so that the guidewires may be inadvertently pulled out of the vessel.

A procedure can often involve the use of two wire/catheter pairs, or sometimes even three or four. Typically, the physician takes up a guidewire and its associated catheter and works with them, then puts them down and takes up a different wire/catheter pair and works with it. In the process, the free ends of the wire/catheter pairs outside the Y adaptor can become wrapped around each other. During a complicated procedure, the free ends of the wire/catheter pairs can become greatly interwoven. The cause of this problem is that the various wire/catheter pairs exit through the same port in the Y adaptor, and that their free ends are more or less free to lie along somewhat parallel paths on the surgical field, hindering adequate identification, control, or organization.

It is an object of the present invention to provide an apparatus which will allow the operator to efficiently identify, organize, and manage two or more pairs of guidewires and their associated catheters. It is also an object of the present invention to provide a device for catheter and guidewire management that can be conveniently secured in place to an operating field.

BRIEF SUMMARY OF THE INVENTION

One system provides a small, firm but pliable pad that can lie on the surgical field, separated from the Y adaptor. The pad can be attached to drapes or some other item in the surgical field, such as by clamping, so as to maintain its desired position relative to the Y adaptor. The pad typically has between two and four pairs of grooves or clamps on it, adapted to hold in place two to four associated pairs of flexible elongated members, with each associated pair of flexible elongated members typically consisting of a guidewire and a catheter. The flexible elongated members in each pair are said herein to be "associated" with each other because the guidewire and the catheter are used together. The grooves or clamps can be arranged in a curved layout, so as to "fan out" the wire/catheter pairs and assist in keeping the free ends of each wire/catheter pair separated from the free ends of other pairs. The grooves or clamps are designed to allow easy insertion and removal of the flexible elongated members. Some of the grooves or clamps can be designed to securely hold a wire or catheter against axial movement, while others can be designed to simply hold a wire or catheter in place relative to the other pairs, without restricting the axial movement of the wire or catheter being held.

The pad can have an adhesive surface on its lower side, to allow it to be adhered to a drape or other item to keep it in place on the surgical field, with a selected separation from, and orientation relative to, the Y adaptor. Other ways to secure the pad or other devices are described below. The adhesive surface can be selectively exposed by removing a peel-off cover. Alternatively, tabs can be provided on the pad, allowing it to be clamped in the desired location and orientation by surgical clamps, or other clamping devices.

The pad can also have labels for identifying each wire and each catheter, or each wire/catheter pair. These can be stick-on type labels, or surfaces adapted for writing upon, or they can be pre-molded labeling areas on the pad, with punch-out circles identifying the selected location of each wire/catheter pair.

Another device for guidewire and catheter management includes a rigid housing having a curved bottom surface for accommodating the shape of a patient's leg. The rigid housing may also have a flat bottom, or may have a bottom in which one portion is flat and another is curved. Flat bottom housings may be appropriate where the device is intended to be placed on an operating or other table instead of on a patient's leg or other curved surface.

In one implementation, the housing includes a number of vertical supports between which are mounted at least one retaining member housing. The retaining member housing may in turn house a retaining member, suitable for receiving and retaining an elongated device such as a catheter or guidewire. The retaining member may have a suitable size, shape, and level of flexibility to allow a catheter or guidewire to be placed therein and held with a desired level of force until a user desires to remove the catheter or guidewire. The retaining member may include one or more slots or grooves for retaining one or more catheters and/or guidewires. Using the device, catheter/guidewire combinations or other such paired devices, or indeed any devices, may be effectively managed in a surgical field.

The device may have one or more attachment mechanisms to allow the same to be secured in an operating field onto, e.g., a fabric such as a towel draping a patient. The attachment mechanisms may be of a number of types of construction, and may include towel clamps with springs or clips, flexible fork assemblies, flexible tabs, hinged tabs, wire capture systems, gripping ring with flexible fingers, wire-and-plug capture systems, and opposing finger towel capture systems.

The novel features of this invention, as well as the invention itself, will be best understood from the attached drawings, taken along with the following description, in which similar reference characters refer to similar parts, and in which:

BRIEF DESCRIPTION OF THE SEVERAL VIEWS OF THE DRAWINGS

FIGS. 8(A)-8(G) illustrate multiple views of a sixth embodiment of a guidewire/catheter management device according to the present invention, employing a ribbed retaining member;

DETAILED DESCRIPTION OF THE INVENTION

Figure 1:
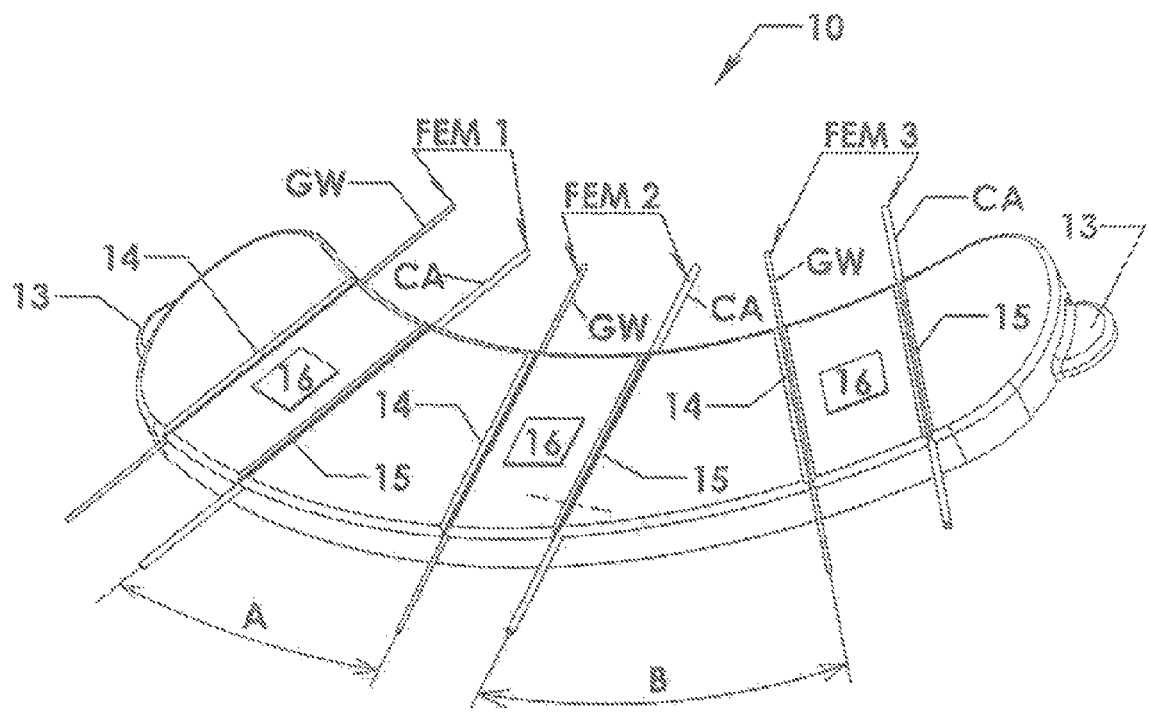
FIG. 1 is a plan view of a first embodiment of a guidewire/catheter management device according to the present invention, utilizing grooves to hold the flexible elongated members.

As shown in FIG. 1, a first embodiment of the device 10 of the present invention includes a pad 12 with a plurality of pairs of grooves 14, 15 in its upper surface. Alternatively, the grooves 14, 15 could be formed in a body of flexible material that is mounted on the pad 12. The pad 12 is constructed of a firm but flexible material. Two or more flat tabs 13 can be formed on the pad 12, to provide surfaces to which surgical clamps can be attached, to hold the pad 12 on a surgical drape, in a selected position and orientation relative to a Y adaptor. Each pair of grooves 14, 15 has an associated label 16, identifying the guidewire GW and the catheter CA that are secured in the respective groove pair. A first pair of flexible elongated members FEM1 can be secured in a first pair of grooves 14, 15, near one end of the pad 12, with a guidewire GW in a first groove 14 and a catheter CA in a second groove 15. Similarly, a second pair of flexible elongated members FEM2 can be secured in a second pair of grooves 14, 15 near the opposite end of the pad 12. Also, if desired, a third pair of flexible elongated members FEM3 can be secured in a third pair of grooves 14, 15 near the center of the pad 12. Further, four or more pairs of grooves 14, 15 can be provided on the pad 12, without departing from the present invention.

The guidewire grooves 14 are preferably slits in the upper surface of the pad 12. The slit can be pushed open and the guidewire GW inserted laterally into the slit, which will then close back around the guidewire GW and hold it in place. That is, this type of groove 14 is designed to grip the guidewire GW and prevent it from moving either in the transverse direction TD or in the axial direction AD, with respect to the groove 14, or relative to the pad 12. This is often preferable with guidewires, since they must be prevented from moving relative to the blood vessel in which they have been placed.

Figure 2:
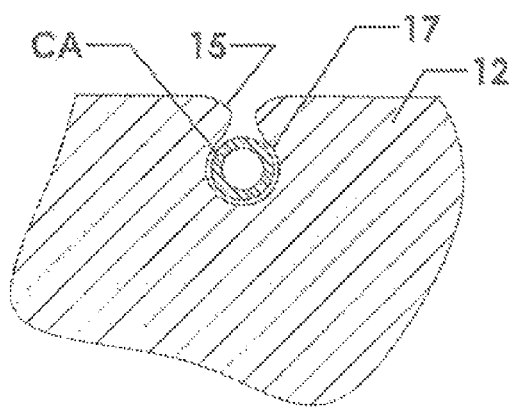
FIG. 2 is a partial section view, showing one type of groove that may be used in the embodiment shown in FIG. 1.

The catheters can also be captured in this slit type of groove, if desired. However, many catheters, being larger in diameter than the guidewires, and carrying larger diameter devices, can be placed in the type of groove 15 illustrated in FIG. 2. That is, rather than a simple slit in the pad 12, this type of groove 15 comprises an open groove, with a tubular cross section 17 below the surface of the pad 12. The surface opening of the groove 15 can be forced open to allow lateral insertion of the catheter CA. Then, the surface opening of the groove 15 will close back around the catheter CA sufficiently to hold it in place against transverse motion relative to the groove 15, or relative to the pad 12. The diameter of the tubular cross section 17 can be selected to closely grip the diameter of the catheter CA, or it can be larger. If the diameter of the tubular cross section 17 fits closely to the catheter CA, it can secure the catheter CA against axial movement relative to the groove 15, and relative to the pad 12. Conversely, if the diameter of the tubular cross section 17 is larger than the diameter of the catheter CA, it can allow the catheter CA to move axially within the groove 15. This can be desirable with some balloon catheters.

The labels 16 can be simply surfaces adapted to be written upon, or stick-on labels with pre-printed identifiers. Or, the labels 16 can be integrally molded into the pad 12, with several possible identifiers listed thereon. These identifiers could include typical guidewire locations, such as LAD, RCA, or CIRC, or even M for Main Artery or B for Branch Artery, etc. Next to each item listed on the label could be a punch-out depression allowing the operator to simply punch a hole next to the item which correctly identifies the location of the associated pair of guidewire and catheter, as the pair is placed in the grooves 14, 15. Alternatively, the operator could simply place a check mark on the label next to the appropriate identifier.

Figure 3:
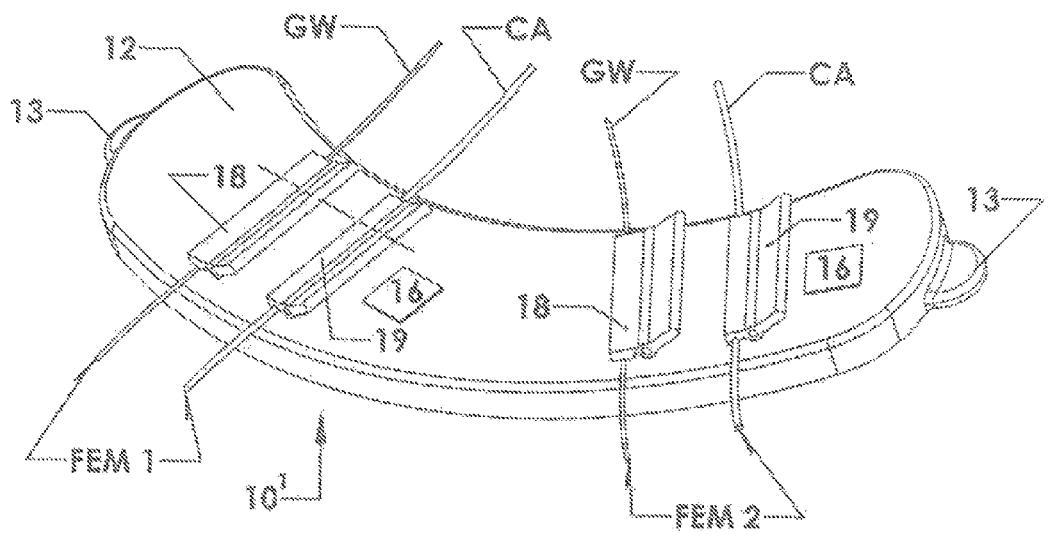
FIG. 3 is a plan view of a second embodiment of a guidewire/catheter management device according to the present invention, utilizing spring clamps to hold the flexible elongated members.
Figure 4:
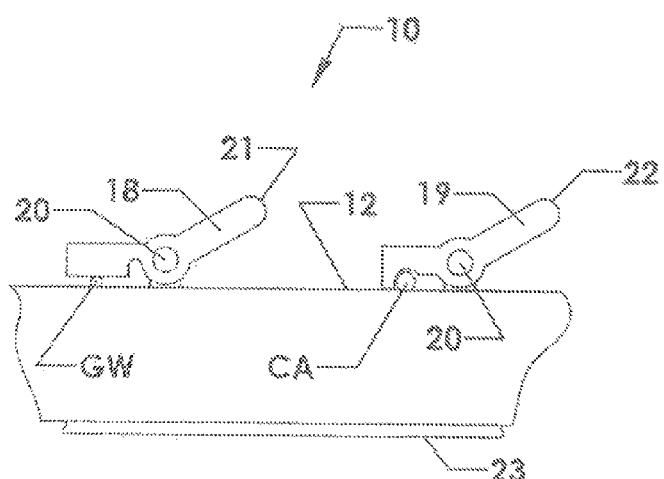
FIG. 4 is a partial edge view of the embodiment shown in FIG. 3.

FIG. 3 shows a second embodiment 10' of the present invention. Rather than grooves in the pad 12, this embodiment utilizes spring clamps 18, 19 to hold the pairs of flexible elongated members in place. That is, the guidewire GW of a first pair FEM1 can be placed in a spring clamp 18 near one end of the pad 12, and the associated catheter CA can be placed in the associated spring clamp 19. Here as before, labels 16 are provided to identify the pair of flexible elongated members that are secured in each pair of clamps 18, 19. FIG. 4 is an edge view of the pad 12 shown in FIG. 3, in a "flattened" view to better illustrate the functioning of the spring clamps 18, 19. A first type of spring clamp 18 could be used to clamp either a guidewire GW or a catheter CA to the pad 12, by simply pressing it against the pad 12. The operator presses down on the wing 21 of the spring clamp 18 to open it, inserts the guidewire GW or catheter CA laterally under the edge of the clamp 18, and releases the wing 21, allowing the clamp 18 to clamp the flexible elongated member tightly against the pad 12. This prevents either transverse or axial movement of the guidewire or catheter relative to the pad 12.

However, another type of spring clamp 19 could also be used where axial movement of the flexible elongated member is desired, such as with some balloon catheters. In this type of clamp, a partial tubular cross-section is provided, within which the flexible elongated member can be placed. As the wing 22 of the clamp 19 is released by the operator, the end of the clamp closes tightly against the pad 12, capturing the catheter CA within the tubular cross-section. If the diameter of the tubular cross-section is larger than the diameter of the catheter CA, the catheter CA is held in place against transverse movement relative to the pad 12, but it is allowed to move axially relative to the pad 12.

The pad shown in FIG. 3 can also have the clamping tabs 13 shown on the first embodiment. Alternatively, or in addition, either embodiment can have an adhesive strip 23 on the bottom of the pad 12, as shown in FIG. 4. The adhesive strip 23 can be covered by a peel-off cover until used. Either method of holding the pad 12 in place is capable of positioning the pad 12 at a desired distance from the Y adaptor, and holding the pad 12 in a desired orientation relative to the Y adaptor.

With either embodiment, it can be seen that the pairs of grooves 14, 15 or the pairs of clamps 18, 19 are arranged in a "fanned" pattern or arrangement on the pad 12, so as to angularly separate or disperse the free ends of the pairs of flexible elongated members FEM1, FEM2, FEM3 from each other. This angular dispersement is illustrated by the angles A, B between the free ends of adjacent pairs of flexible elongated members in FIG. 1.

FIGS. 5(A)-5(G) illustrate a third embodiment 30 of the present invention; a guidewire 80a and catheter 80b are illustrated as being retained by the device (these elements are in FIGS. 6-8). In this embodiment, a number of gripping components 24a, 24b, 24c, etc., are mounted on a top surface 34 of a housing 40. The housing 40 may have a curved base 26 so that if the housing 40 is placed on a patient, the curved base 26 will fit comfortably and securely on the patient's leg or the like. An attachment mechanism 50 is also illustrated, the attachment mechanism 50 including two opposing fingers 28 and 32, between which a towel draping the patient may be inserted to hold the device 30 in place. A series of teeth are illustrated at the ends of fingers 28 and 32 to further assist the gripping of a towel. Other types of attachment mechanisms are described below with respect to FIGS. 9-16.

Figure 5A:
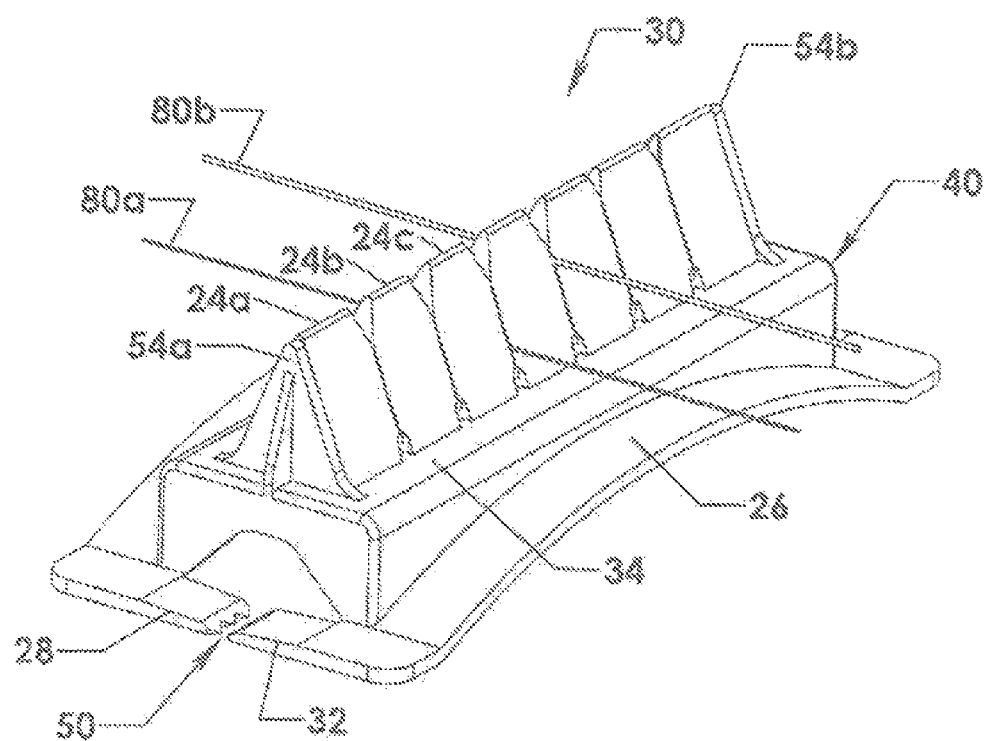
FIGS. 5(A)-5(G) illustrate various views of a third embodiment of a guidewire/catheter management device according to the present invention.
Figure 5B:
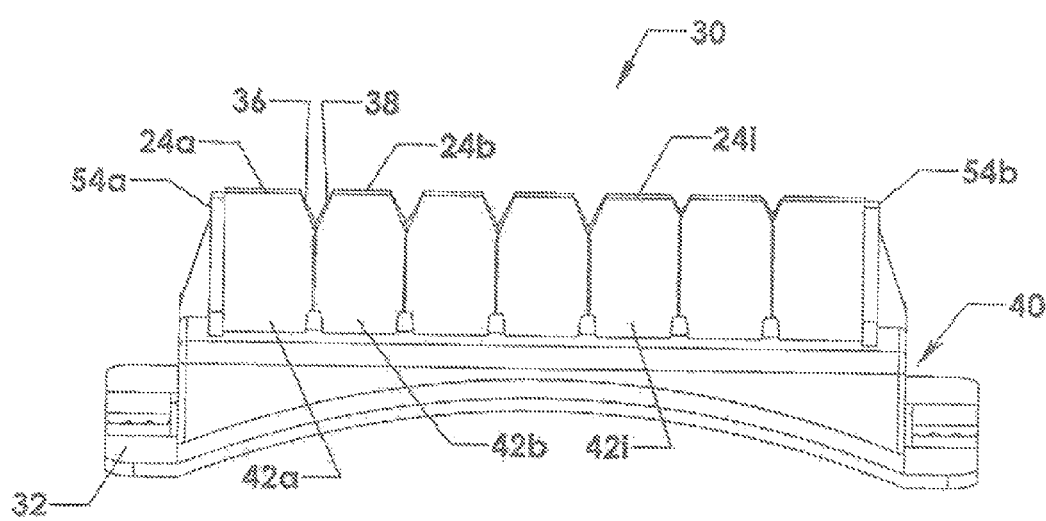
Figure 5C:
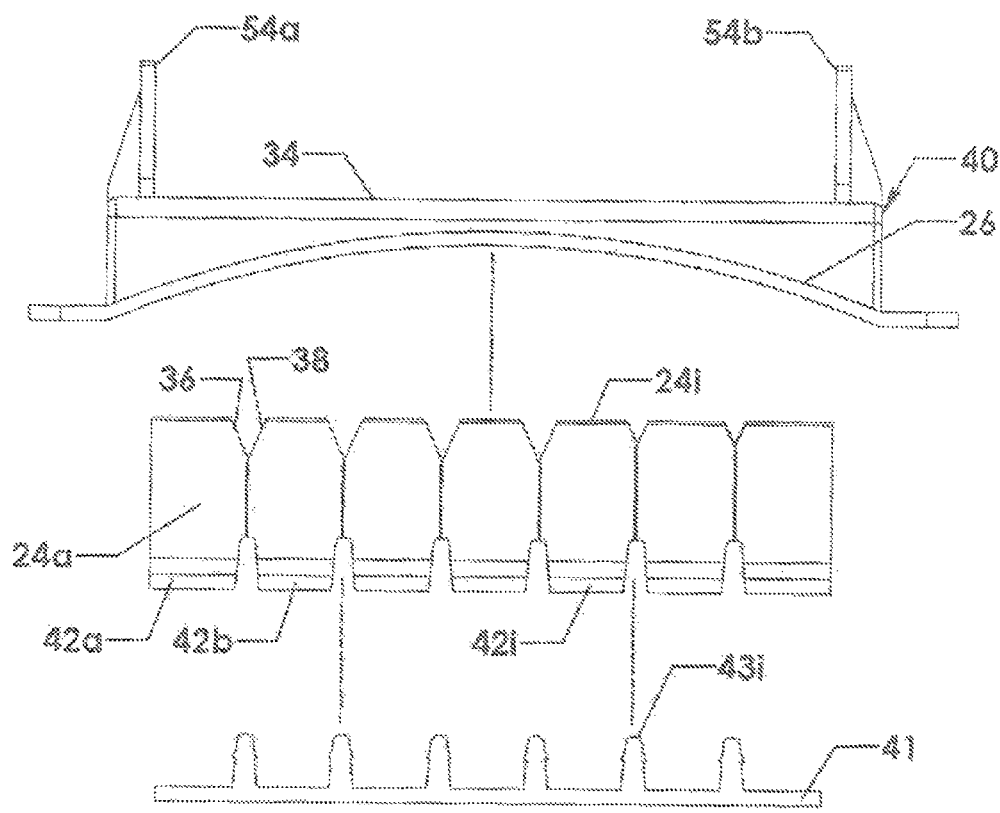
Figure 5D:
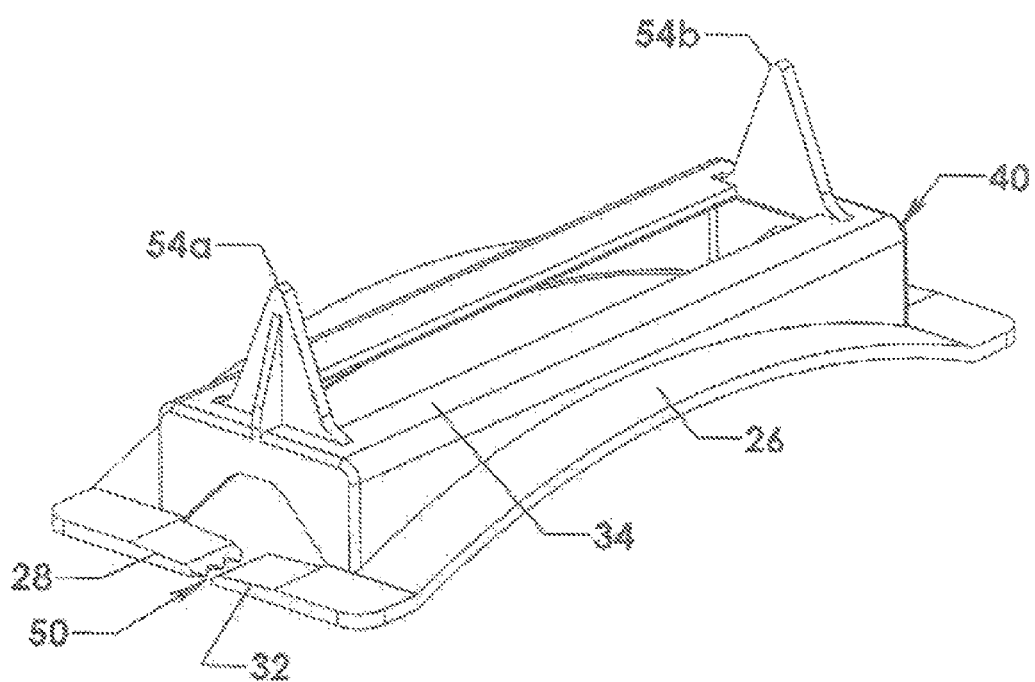

Referring in addition to FIG. 5(C), the gripping components 24a, 24b, etc., include various features to allow their mounting in the top surface 34 as well as to allow a catheter or guidewire to be inserted and gripped between the components, i.e., frictionally held within the gap between component 24a and component 24b.

Figure 5E:
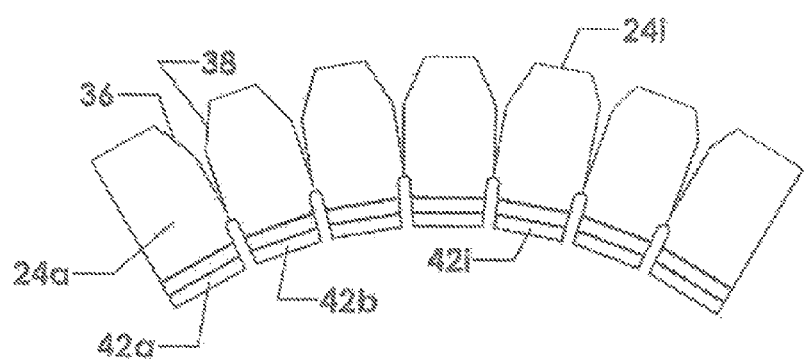

To hold the gripping component 24i on the housing, a snap-fit device 42i (FIG. 5(E)) may be employed to frictionally and mechanically hold the component 24i to the housing 40. A strip 41 with plugs 43i may be employed to give further support to components 24i, as well as to assist in the centering, placement, and retention of components 24i in the housing 40. A variety of other devices and techniques will be understood to be employable to retain component 24i on the housing, given this teaching. In addition, to assist the placement of a catheter or guidewire within the gap, the tops of the gripping components 24a, 24b, etc., may include surfaces 36 and 38 which are configured to form a "V" when placed next to each other, as shown in FIGS. 5(B), 5(C), 5(E), and 5(F). The "V" shape makes placement of a catheter or guidewire highly convenient for a nurse or physician.

Figures 5F, 5G:
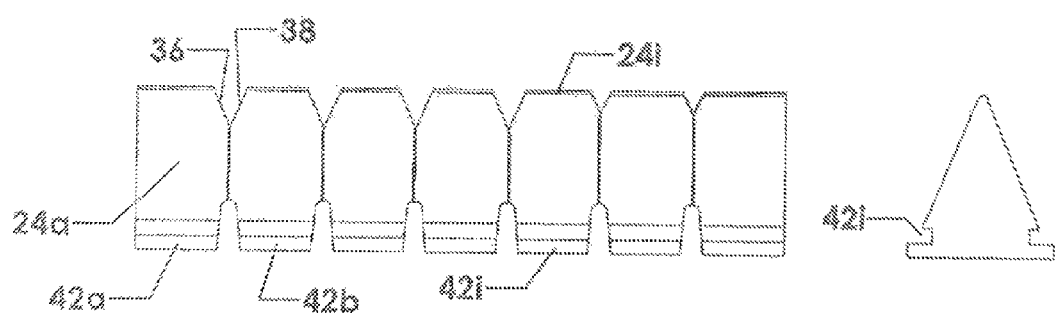

The cross-section of the components 24i may be seen in FIG. 5(G). The benefits of a substantially or generally triangular cross-section are described below.

In one manufacturing method, a molded silicone (or other suitable material) rod of triangular end profile may be cut or sliced to form the slots or grooves.

Another manufacturing method takes advantage of vertical supports 54a and 54b. That is, as illustrated in FIG. 5(C), vertical supports 54a and 54b may be employed to hold the group of components 24i to the housing. The vertical supports 54a and 54b may be particularly important when the components 24i are formed in an open mold process, which results in a molded part that resembles FIG. 5(E), that is, such that the slit or groove is in a substantially open configuration. The part takes the proper shape, such that the slots are in a closed configuration, when the part is compressed and inserted into the housing 40. This method of manufacturing has a high degree of accuracy and repeatability.

In more detail, the part is molded as shown in FIG. 5(E), and the flexible properties of elastomers allow for a small hinge point at generally the base of the slit. The slit may then be designed "open", such that the injection mold may carry a core of sufficient strength to withstand cavity injection pressures of 15,000-20,000 psi. In some cases, it may be difficult to mold the slit such that the same is "closed", as the minimum thickness (0.020, or 0.5 mm) blade forming the core may generally not take the pressure and may generally be too thick.

In some cases, the stiction or "grab" on the wires may be excessive when an elastomer, e.g., TPE, is used, rather than silicone. A solution, described below in relation to FIGS. 8(A)-8(G), is to use a ribbed slot, which has less surface area. In addition, ribs allow for a strong and easily-fabricated core for the injection mold. Whether ribs are used or not, an angle between the faces may be 0, 1, 2, 3, 4, or more degrees, as well as values in between.

For elastomeric materials, it is noted that the material properties of an elastomer are such that the same may "cold-flow", or form itself around the surface of an intruding member, such as a guidewire. It is minimal on a larger diameter wire as there is less surface area of the wire relative to the material property, or Shore. Cold-flow is more pronounced over a smaller surface area for a small diameter guidewire. There is a balance of stiction between large and small wire diameters. There is less surface area in the upper half of the slit where a larger wire would nominally be used (there is a natural "tactile" sense as to maximum depth) due to a smaller triangular end profile. There is increasing surface area (applied generally to the wire) in the lower half of the slit where the smaller wire is used, due to the larger surface area provided by the triangular end profile. The result is that the design tends to balance out the stiction, or grab, of various wire diameters.

A fourth embodiment 50 is illustrated in FIGS. 6(A)-6(E), in which a housing 51 includes a plurality of vertical supports 78*a*-78*d*, each of which extends upward from a top surface 48. Each vertical support 78*a*-78*d* can extend from a respective support base end 801 to a respective support top end 803. Sequential or adjacent support base ends 801 (e.g., support base ends 801 of vertical supports 78*a* and 78*b*) and a connection member 809, which connects the sequential support base ends 801, can define a retaining member housing 811 having a closed base 813. Between the at least two vertical supports 78*a*, 78*b*, etc. and within one or more retaining member housings 811, are disposed one or more retaining members 82*a*-82*c*. Each retaining member 82*a*-82*c* can extend from a respective member base end 805 to a respective member top end 807. It will be understood that the number of vertical supports and the number of retaining members can vary widely. By this modular construction, different retaining members may be switched out and replaced according to the requirements of the user. In addition, the pliable nature of the retaining members is reinforced by the more rigid retaining member housing. Each retaining member may include one, two, or more slots or grooves in which flexible elongated members such as catheters or guidewires may be placed and retained (two slots are shown).

The housing 51 may have a curved base 52 so that if the housing 51 is placed on a patient, the curved base 52 will conform to and fit comfortably and securely on the patient's leg or the like. The curved base 52 may have a bottom surface that includes protuberances, which help to grip the towel and further prevent movement of the device 50. The protuberances are generally formed on a bottom surface of the housing or body. In cases where the housing 51 is placed on the table itself, the components forming the housing, and/or an optional attachment mechanism, are provided at least partially with a flat base 111 to accommodate the flat table. Of course, in some implementations, the entire device may be designed to be flexible so that the user may bend the device around the patient's leg or other limb, to fit a variety of limbs. It is also noted that the top surface 48 may be curved. The curved base may work with the various attachment mechanisms described to fully secure the catheter and guidewire management device to a patient.

Figure 6A:
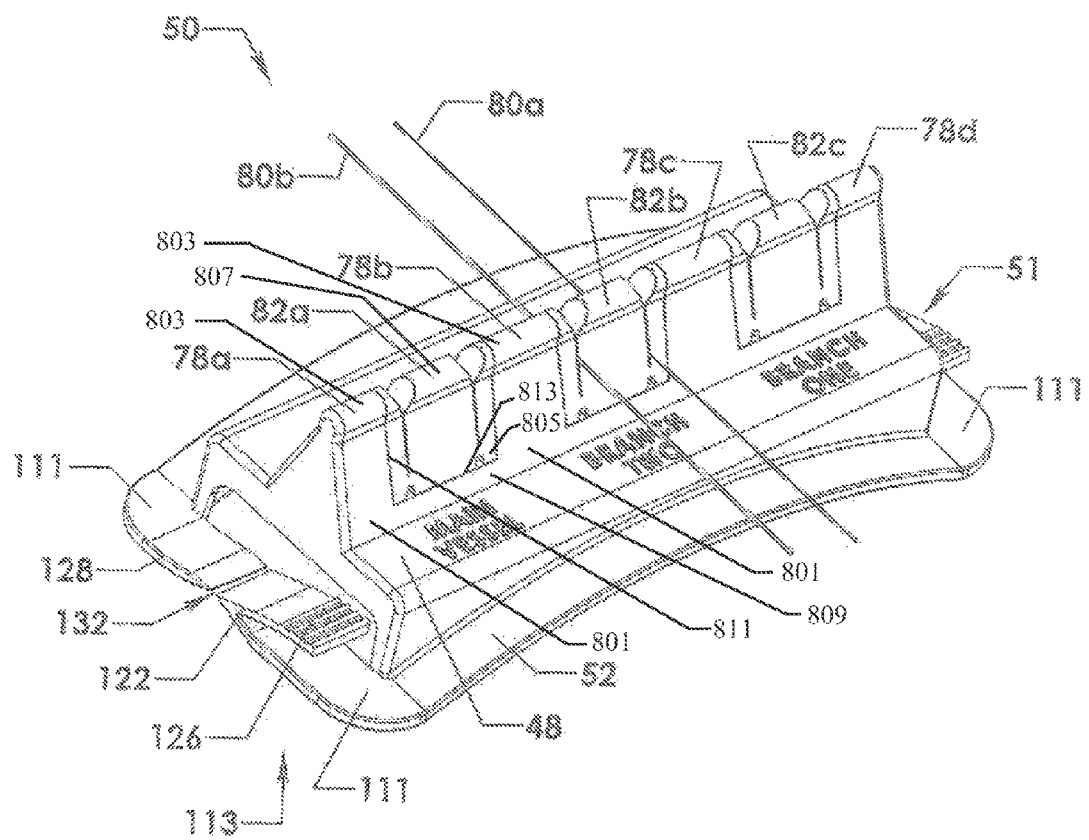
FIGS. 6(A)-6(E) illustrate multiple views of a fourth embodiment of a guidewire/catheter management device, according to the present invention.
Figure 6B:
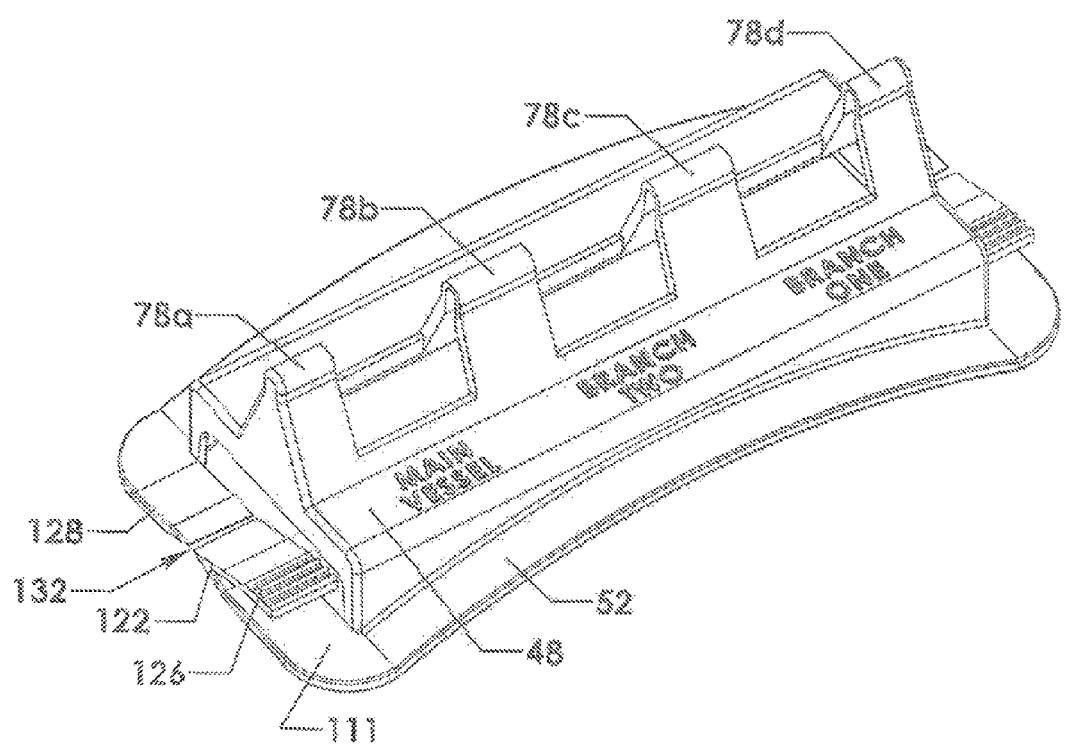
Figure 6C:
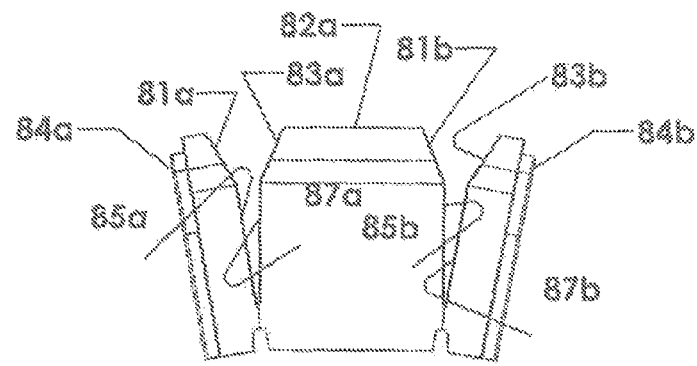
Figure 6D:
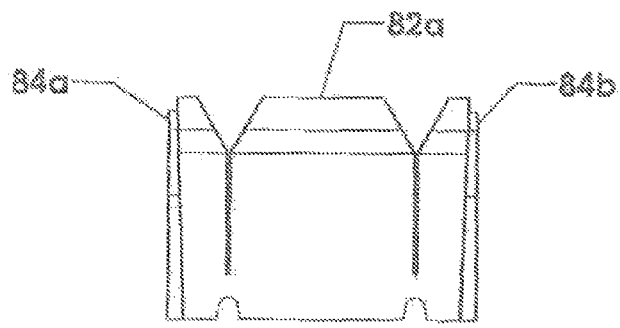
Figure 6E:
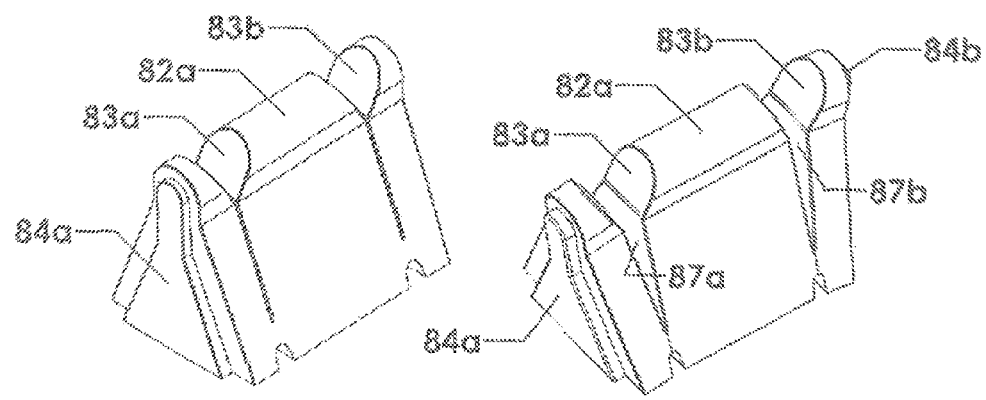

Referring in particular to FIGS. 6(C) and 6(E), the retaining members 82*a*-82*c* include various features to allow the same to be mounted in the supports 78*a*-78*d* as well as in the top surface 48 of the housing 51. Referring to FIGS. 6(C)-6(E), to hold the retaining members within the housing, fitted end components 84*a* and 84*b* may be employed. The fitted end components cooperate with the vertical supports to frictionally hold the retaining members to the housing. A variety of other devices and techniques will also be understood to be employable, given this teaching.

The retaining members also have features to accommodate a catheter or guidewire such that the same may be inserted and gripped within the retaining member, i.e., frictionally held within a gap defined in or by the shape of the retaining member.

Slots may differ in their taper (not shown). One may have a pronounced taper, and one may have a very small taper. Larger tapers may be appropriate for many catheters (with a typical size being on the order of 0.020 to 0.040 inches), while smaller tapers may be appropriate for many guidewires (with a typical size being on the order of 0.014 inches). This is of course highly arbitrary, and any combination of retaining members may be employed, including systems with only one type of retaining member.

To assist the manufacturing process, the retaining members 82*a*, 82*b*, etc., may be molded in an open form, shown in FIG. 6(C) as well as the right-hand side of FIG. 6(E). This open mold process is described above in connection with FIG. 5(E) and is not repeated here.

To assist the placement of a catheter or guidewire within the slot, the tops of the slots in the retaining members 82*a*, 82*b*, as shown in FIG. 6(C), may be configured to form an entry angle, such as the "V" as shown. The entry angle may be, e.g., 30-45 degrees and about 3 mm in depth; these values can vary widely. The entry angle may transition smoothly into the slit or groove in which the catheter or guidewire is held. In more detail, the retaining member 82*a* includes surfaces 81*a*, 81*b*, 83*a*, and 83*b* which form a wide "V" shape that may be used by a nurse or physician to conveniently locate the catheter or guidewire in the retaining member. The surfaces 81*a*, 81*b*, 83*a*, and 83*b* terminate at surfaces 85*a*, 85*b*, 87*a*, and 87*b*, which are generally the surfaces that engage with the catheter or guidewire. While shown as flat surfaces, these surfaces may be provided with a variety of curvatures to achieve various retaining effects, e.g., to provide extra retention power, lessened retention power, or the like. The surfaces 85*a*, 85*b*, 87*a*, and 87*b* may form a zero angle or may form a nonzero angle "a", which may be, e.g., 2-10 degrees, e.g., 4 degrees. The force exerted by these surfaces on a catheter or guidewire may vary as the catheter or guidewire is pressed down into the retaining member. If the catheter or guidewire is inserted a small distance, less holding force will be exerted than if the catheter is inserted a large distance.

The holding force may be varied not just because of the taper or angle "a", but also because of the triangular shape (in cross-section) of the retaining member. That is, another way to vary the force is by the amount of retaining member holding the catheter or guidewire. As the catheter or guidewire is pressed down into the device, the amount of retaining member frictionally contacting the same is increased, increasing the holding force. This has a number of beneficial aspects.

In particular, sometimes a physician desires that the wire or catheter be held very tightly so that the same does not move; at other times, the physician desires to be able to slide the catheter back and forth for precise placement. For example, to open an artery, first a guidewire is threaded down the vessel. Then a catheter with a balloon or metal stent at its tip is threaded onto the wire and advanced into the artery to the target blockage. Often, more than one artery is treated. Very commonly, blockages form at branch points, so the operator has to insert two wires, one into each branch, and then thread two balloons or two stents over the two wires so that both wires and both balloons (or stents) are across both branches simultaneously. Before inflating the balloons (or deploying the stents), the operator needs to carefully advance and retract each balloon, while watching their positions on x-ray fluoroscopy, to get the devices in a precisely desired position. Often, a physician will push one balloon down the artery and, although not desired, the other moves down with it and vice-versa. In addition, it is difficult to remember which wire and catheter is going down which branch. Moreover, the wires and catheters may be inadvertently wrapped around each other, making changing out one catheter for another difficult, if not impossible. With the disclosed devices, an operator can push the wires all the way down into the slot so they are held tightly but keep the balloon or stent catheters at the top of the slot so they stay in position with respect to each other (but can still be moved in and out).

Referring back to FIG. 6(A), the device 60 may include an attachment mechanism 113, shown in FIG. 6(A) as an assembly of opposing fingers. The assembly includes a first finger 122 separated by a substantially opposing finger 128. Distal ends of the fingers 122 and 128 are separated by a gap 132. A portion of one or both fingers 122 and 128 may include ribs 126 for ease in gripping. In the structure of FIG. 6(A), only one finger (finger 122) (per set) is shown with ribs 126.

In use, a towel may be drawn into the gap 132 and held in place by frictional engagement with fingers 122 and 128. To remove, the gap 132 is made larger to allow the towel to escape the frictional engagement. In the configuration of FIG. 6(A), one way to increase the size of the gap 132 is to push on the ribs 126, thereby deflecting a distal tip of the finger 122. Other ways of increasing the size of this gap will also be understood, given this teaching.

Other types of attachment mechanisms are disclosed below with respect to FIGS. 9-16.

FIGS. 7(A)-7(F) illustrate a fifth embodiment 60 of a guidewire/catheter management device. In this embodiment, certain elements are similar to those described above with respect to FIGS. 6(A)-6(E), and these elements have been given the same reference numerals and are not further described here.

Figure 7A:
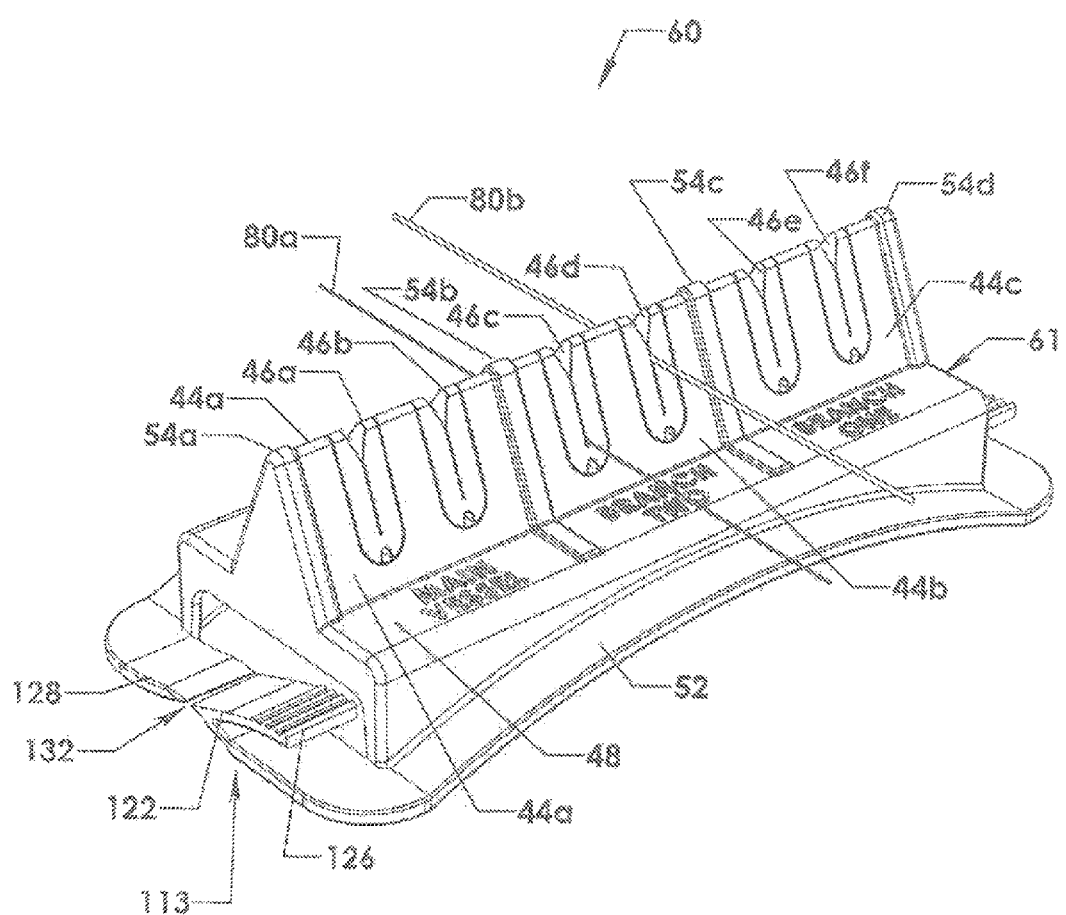
FIGS. 7(A)-7(F) illustrate multiple views of a fifth embodiment of a guidewire/catheter management device, according to the present invention.
Figure 7B:
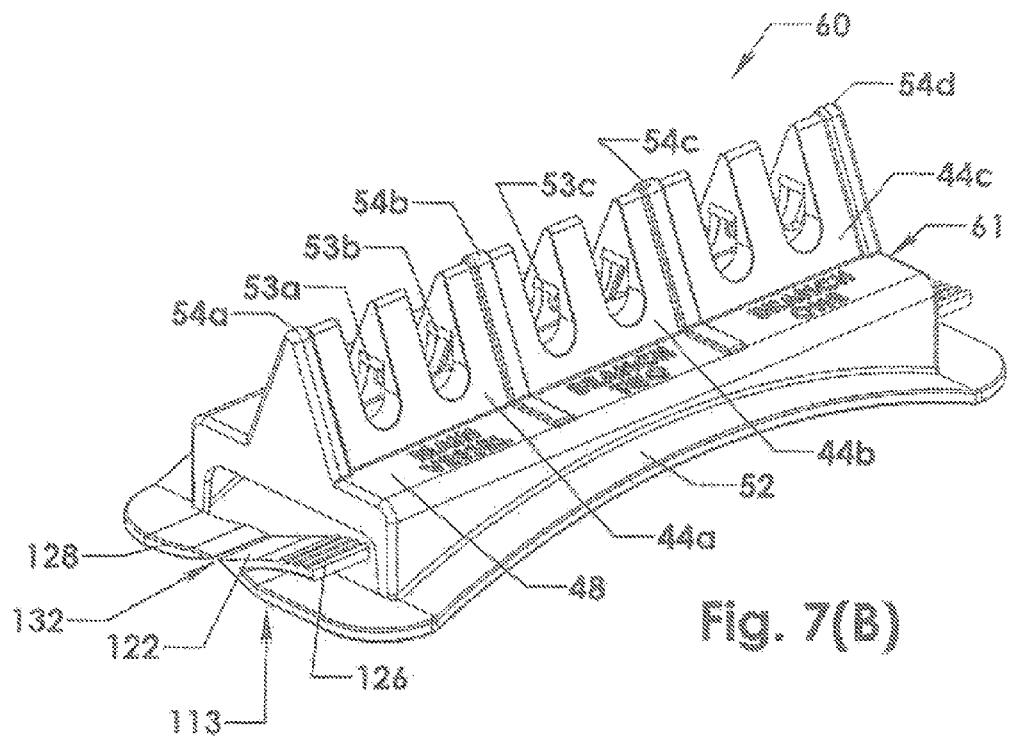
Figure 7C:
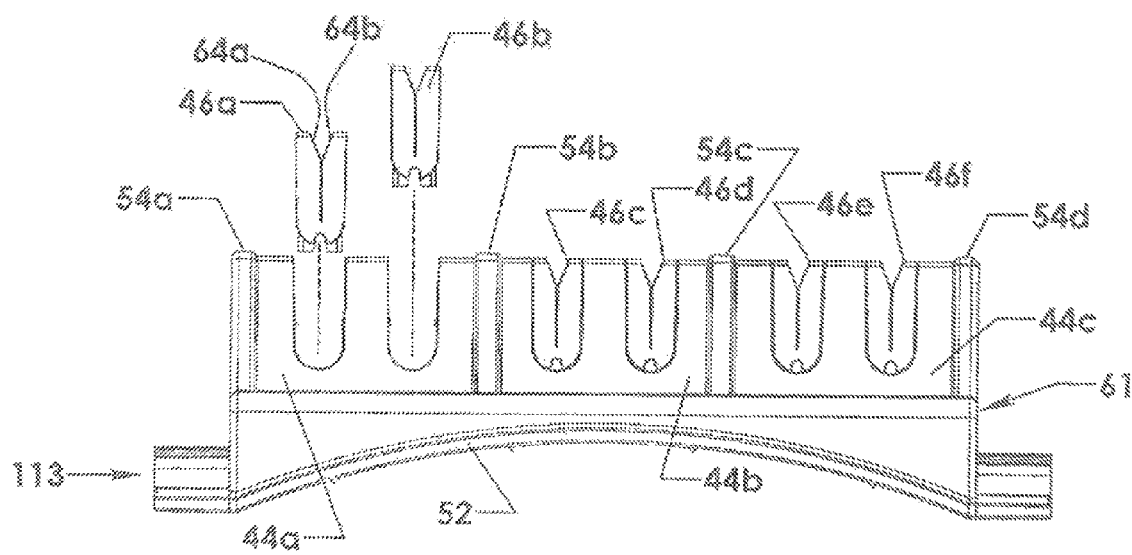
Figure 7D:
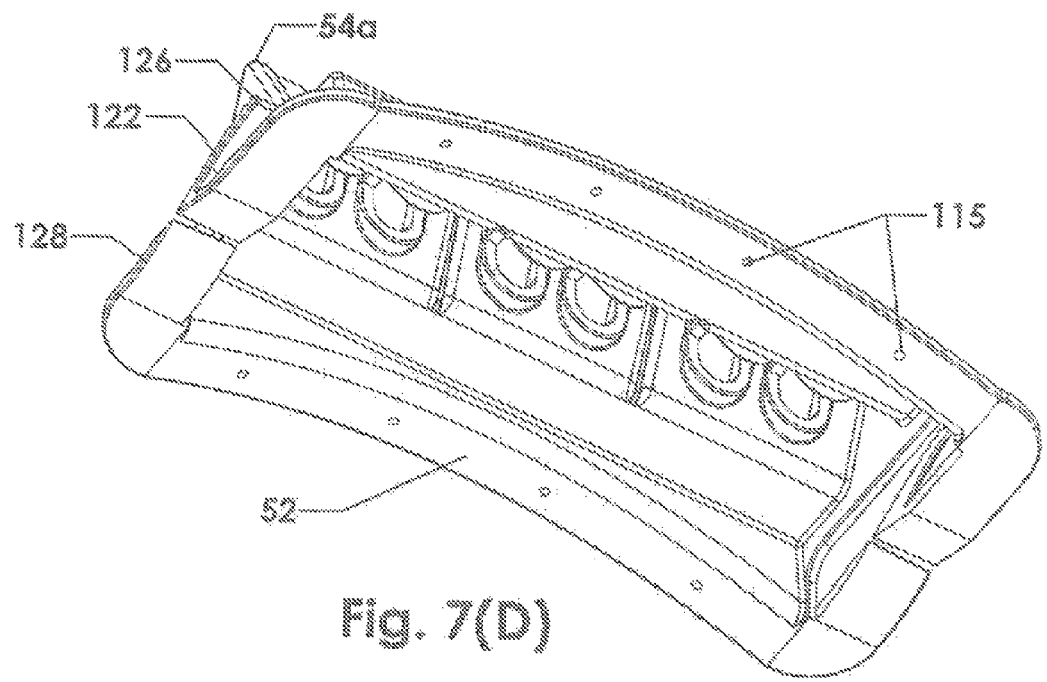
Figure 7E:
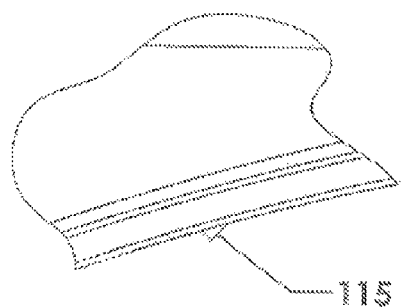
Figure 7F:
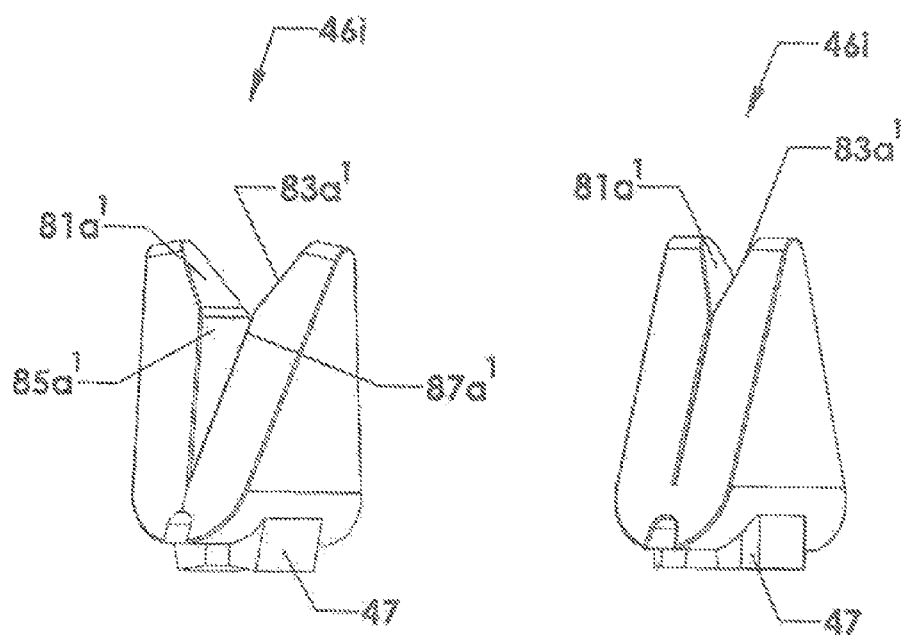
Figure 8A:
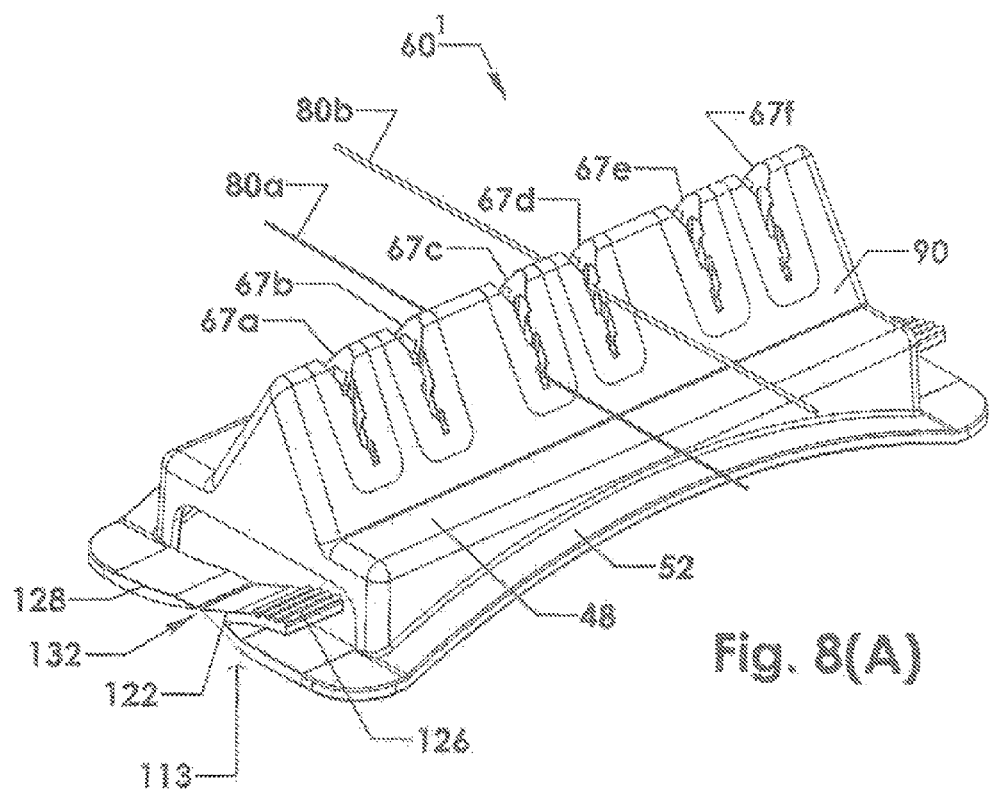
Figure 8B:
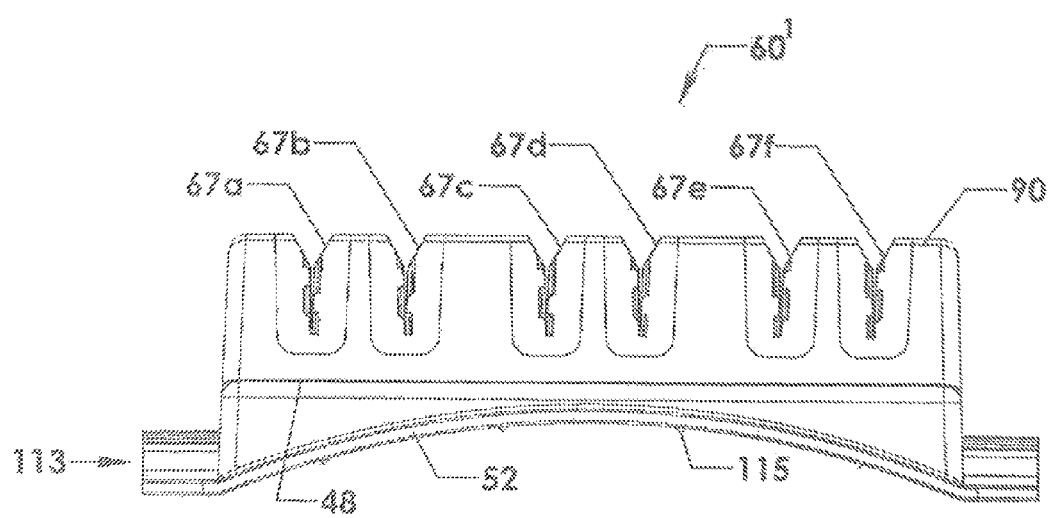

In this fifth embodiment, the device 60 has a housing 61 with a top surface 48 from which extend vertically upward a number of supports 54a, 54b, etc. A number of retaining member housings 44a-44c are illustrated as mounted in the housing 61. A number of retaining members 46a-46f are illustrated mounted in the retaining member housings. In many cases, the retaining member housings may be formed integrally with the housing 61. As shown in FIG. 7(C), the retaining members 46i may be inserted into the retaining member housings via snap-fit components 47 (shown in FIG. 7(F)). Also as shown in FIG. 7(F), the retaining members may be formed using the open mold process described above in connection with FIG. 5(E), with the benefits appertaining thereto. FIG. 7(F) also illustrates details of the slot and groove which are generally the same as described above in connection with FIGS. 6(C)-6(E), are given corresponding (and primed) reference numerals, and are thus not further described here. Finally, FIGS. 7(D) and 7(E) illustrate a number of protuberances 115, which can serve to further secure the device to an operating table or to a towel draping a patient.

FIGS. 8(A)-8(E) illustrate a number of views of a sixth embodiment of a device 60' for catheter and guidewire management, having a housing 90 with vertical supports 91a-91g. In this device 60', retaining members 67a-67f with ribbed slots or grooves are employed. Certain elements are similar to those described above with respect to FIGS. 6(A)-6(E), and these elements have been given the same reference numerals and are not further described here.

Details of the ribbed retaining members 67i are shown in FIGS. 8(E)-8(G). The retaining member 67i includes fingers 72a and 72b. The finger 72a includes a rib 74a and an indentation 76a, while the finger 72b is shown with a rib 74b and an indentation 76b. The rib 74a fits into the indentation 76b while the rib 74b fits into the indentation 76a. In this way, a catheter or guidewire may be held even more securely, while minimizing the effects of "healing", described in greater detail below. Such retaining members 67i may be conveniently manufactured using the open mold process described above in connection with FIG. 5(E).

It is noted that the materials constituting the retaining member may be, e.g., elastomeric materials such as a molded rubber or silicone. While the entire shape may be molded, in some implementations, knife slits may be made into the retaining members to form the surfaces described above. The durometer of the silicone or rubber may vary, e.g., in the range 30-80 Shore hardness, although this range is purely exemplary and other values are also possible. The materials constituting the housings and attachment mechanisms may be, e.g., an injection-molded plastic, silicone, or rubber. It will be understood that other materials are also contemplated. One aspect important in material choice is "healing", which is the tendency, especially of like materials, to adhere to each other upon constant contact, e.g., when stored for long periods of time. In the ribbed slot examples above, it may be desired to configure the same such that the ribs and indentations fit closely but do not touch, even when wires and catheters are removed. In this way, the amount of deleterious "healing" may be lessened. In addition, molded slits may be less susceptible to such healing.

The slits of the retaining members may be such that they are about 1 cm apart, as well as 1-2 cm above the operating field, so as to not interfere with the physician's hand motions. Of course, these distances may vary widely depending on the application. While the retaining members are described as generally triangular in shape (in a cross-section viewed perpendicular to a plane bisecting the two surfaces 62a and 62b), it will be understood that any shape with a similar change in dimensions may be employed, e.g., parabolic or the like. Retaining members that are only substantially triangular are also envisioned. Retaining members may be used with just one slit or groove, and the entire device may have just one slit or groove; such embodiments may be particularly useful for temporary holding of guidewires or the like.

Figure 9A:
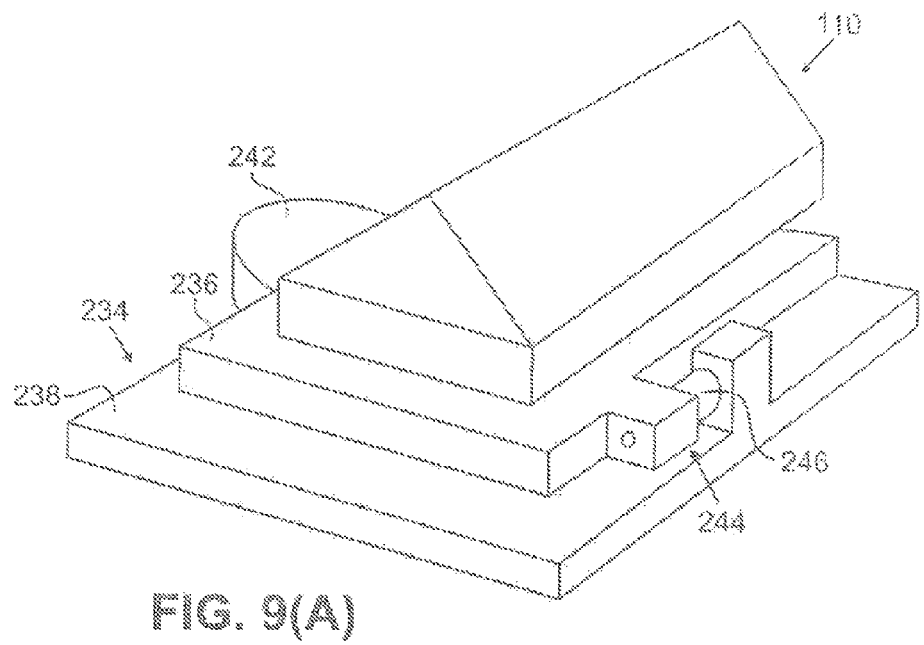
FIGS. 9(A) and 9(B) are perspective and side views, respectively, of a first embodiment of an attachment mechanism for attaching a device to a towel, e.g., as may be draping a patient during surgery, here implemented as a towel clamp with spring.
Figure 9B:
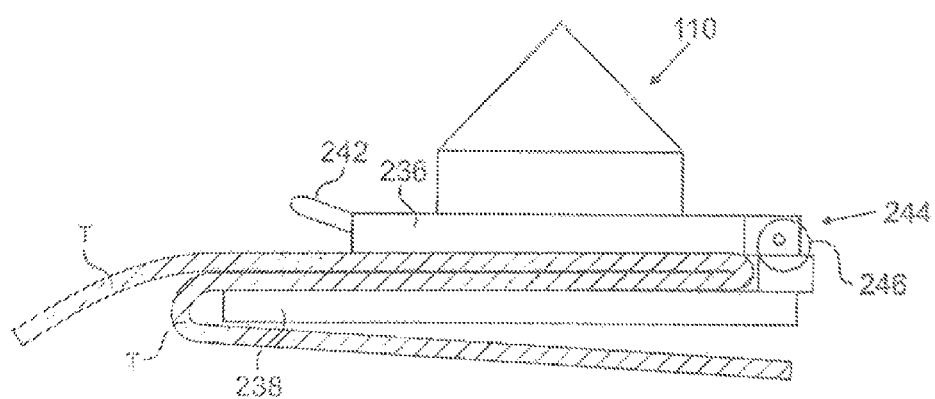

FIGS. 9(A) and 9(B) are perspective and side views, respectively, of a first embodiment of an attachment mechanism for attaching a device to a towel, e.g., as may be draping a patient during surgery, here implemented as a towel clamp with spring. In particular, a device 110 is illustrated that has a construction as described above with respect to any of the elongated member management devices. The device 110 is mounted to or formed integrally with an attachment mechanism, which in this case is a towel clamp with spring assembly 234. The towel clamp with spring assembly 234 includes an upper plate 36 and a lower plate 238 which are attached via a hinge assembly 244 which may include a spring 246. A pull tab 242 may extend from one extremity of the upper or lower plate (or both) for ease in attaching (and disengaging) the towel clamp from a towel T.

In use, a towel T is placed between the upper and lower plates. The spring forces the upper plate towards the lower one, frictionally securing the device 110 to the towel T. At any time, for installation or for removal, the pull tab 242 may be used to separate the upper from the lower plate.

Figure 10A:
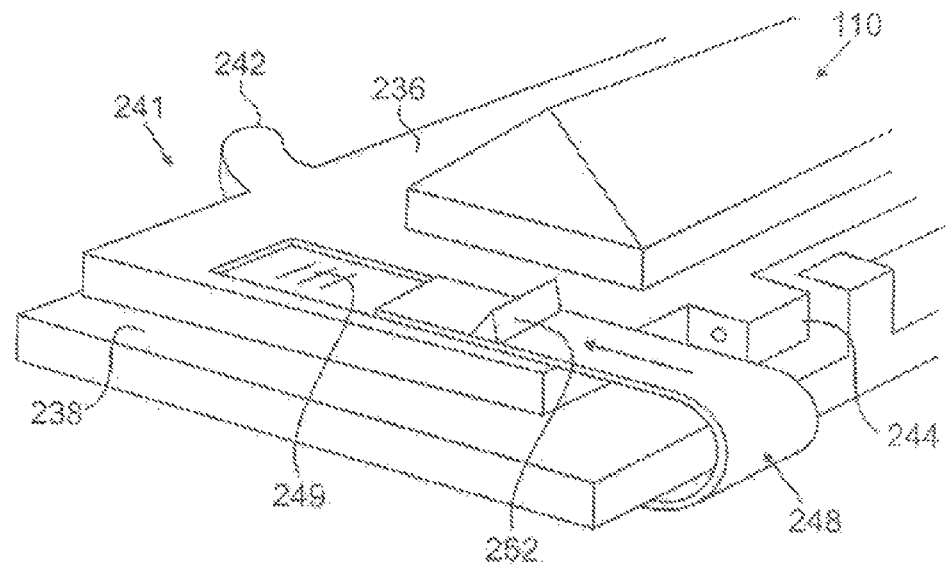
FIGS. 10(A) and 10(B) are perspective and side views, respectively, of a second embodiment of an attachment mechanism for attaching a device to a towel, e.g., here implemented as a towel clamp with clip.
Figure 10B:
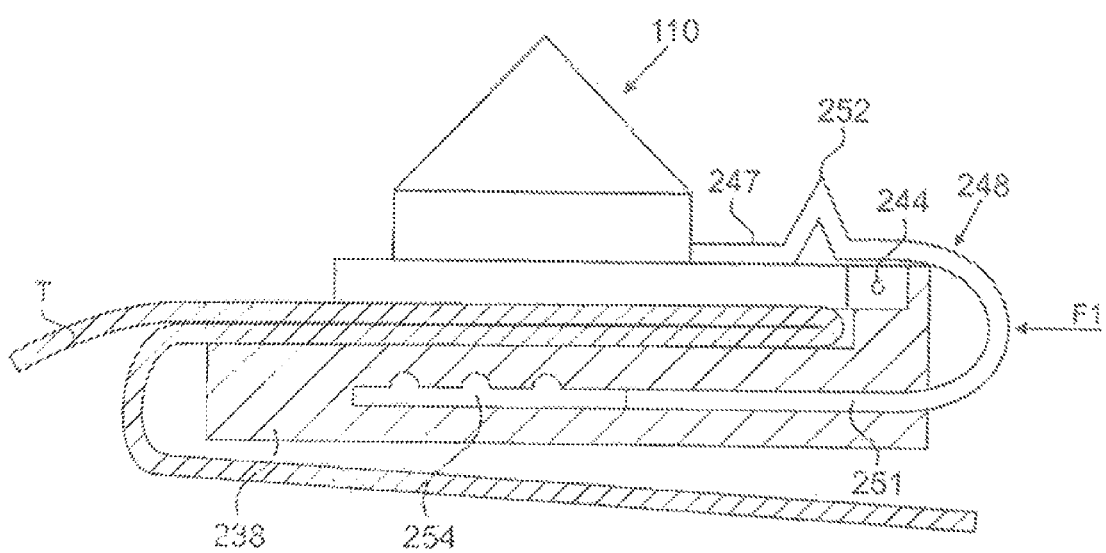

FIGS. 10(A) and 10(B) are perspective and side views, respectively, of a second embodiment of an attachment mechanism for attaching a device to a towel, e.g., here implemented as a towel clamp with clip. In particular, a device 110 of the above-described construction is mounted on or formed integrally with an attachment mechanism, shown in FIGS. 10(A) and 10(B) as a towel clamp with clip 241. Some elements are the same as in FIG. 9. For example, an upper plate 236 is coupled to a lower plate 238, and a pull tab 242 may extend from either (in FIGS. 10(A) and 10(B), from the upper plate). A hinge assembly 244 allows hinged movement of the plates. However, one of ordinary skill will recognize that the hinge assembly 244 is not necessary in all of these embodiments. For example, in FIGS. 10(A) and 10(B), the clip itself, as described below, may in some constructions be enough to hold the upper plate attached to the lower plate.

Referring again to FIGS. 10(A) and 10(B), a clip 248 is shown, which holds the upper plate to the lower plate. The clip 248 may ride in an optional track 249 for ease of placement. An internal slot 254 may also be employed such that the clip 248 has a lower arm 251 that enters the lower plate. The internal slot 254 is only shown in FIG. 10(B). It will be recognized that the track or internal slot may be employed on either the upper or lower plates, or both. However, in many implementations, it is easier to remove the clip if at least one plate does not employ an internal slot. For additional ease of installation and removal, a corrugation 252 may be disposed on an upper arm 247 of the clip 248.

For installation, a towel T is placed between the upper and the lower plates and the clip loaded into the track and/or internal slot (or just around the plates if neither a slot nor a track is employed). Force applied in the direction F1 secures the clip to the plates, and this secures the device 110 to the towel T.

Figure 11A:
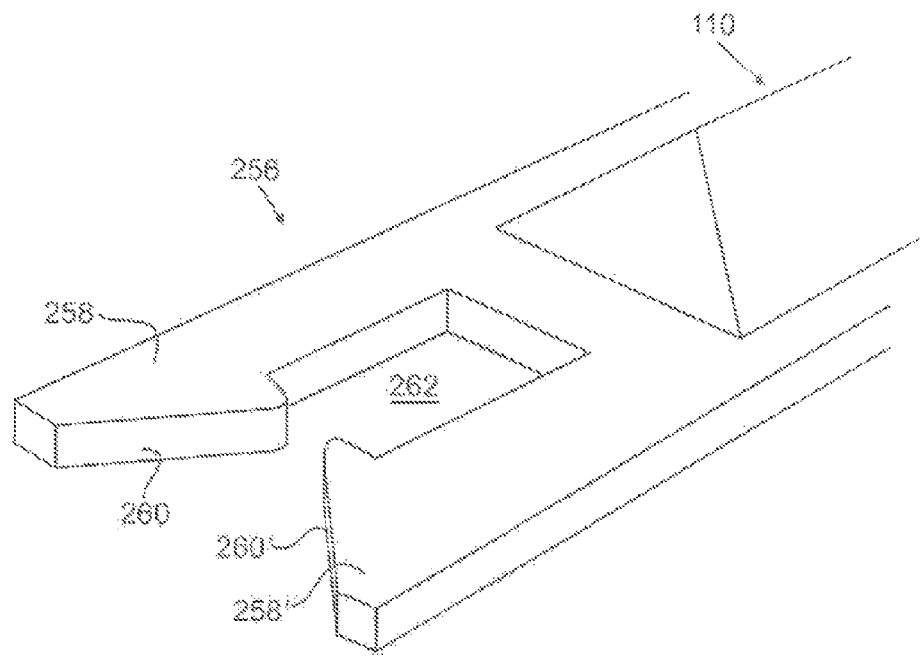
FIGS. 11(A) and 11(B) are perspective and side views, respectively, of a third embodiment of an attachment mechanism for attaching a device to a towel, e.g., here implemented as a flexible fork assembly, which may be employed with or without a spring.
Figure 11B:
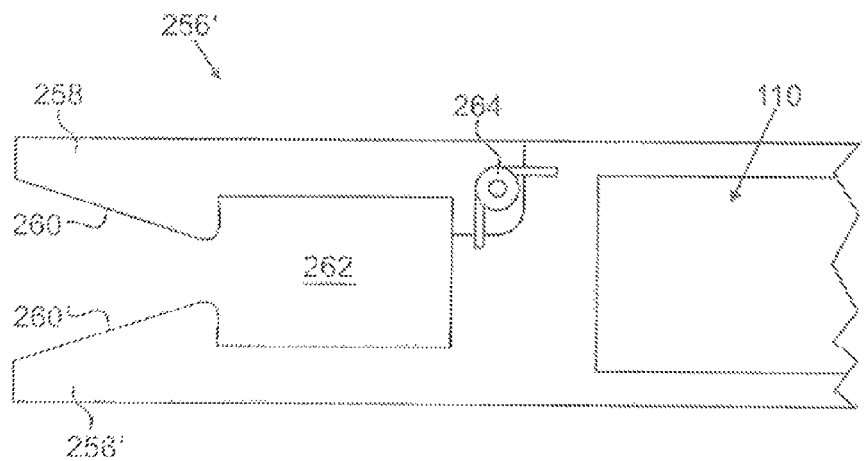

FIGS. 11(A) and 11(B) are perspective and side views, respectively, of a third embodiment of an attachment mechanism for attaching a device to a towel, e.g., here implemented as a flexible fork assembly. In particular, FIG. 11 shows a flexible fork assembly 256, which may be employed with (FIG. 11(A)) or without (FIG. 11(B)) a spring.

At least two tines 258 and 258' may form the fork 256. One or more tapered surfaces 260 and 260' may be employed to ease introduction of the towel portion into a hole 262 defined by the tines 258 and 258'.

In the implementation of FIG. 11(A), in use, the flexibility of the tines themselves may be configured to be enough to, upon installation of a towel portion, distend the tines and then bring the same back together to securely hold a towel.

In a related implementation, that of FIG. 11(B), a flexible fork assembly 256' is shown including a spring 264 attached to the tine 258. In a related implementation, a spring may be attached to the tine 258' as well. In these implementations, the flexibility of the fork tines is assisted by the angular resilience of the spring.

In use, a towel portion may be inserted into hole 262, and the same may be conveniently inserted through the use of tapered surfaces 260 and 260'. Generally, a sufficiently-large portion of the towel is inserted so that a sufficient friction-fit is achieved, such that the towel does not pull out of the hole. This requirement can also be employed to set the minimum spring constant (or stiffness) of the spring 264, in implementations where this element is used.

Figure 12A:
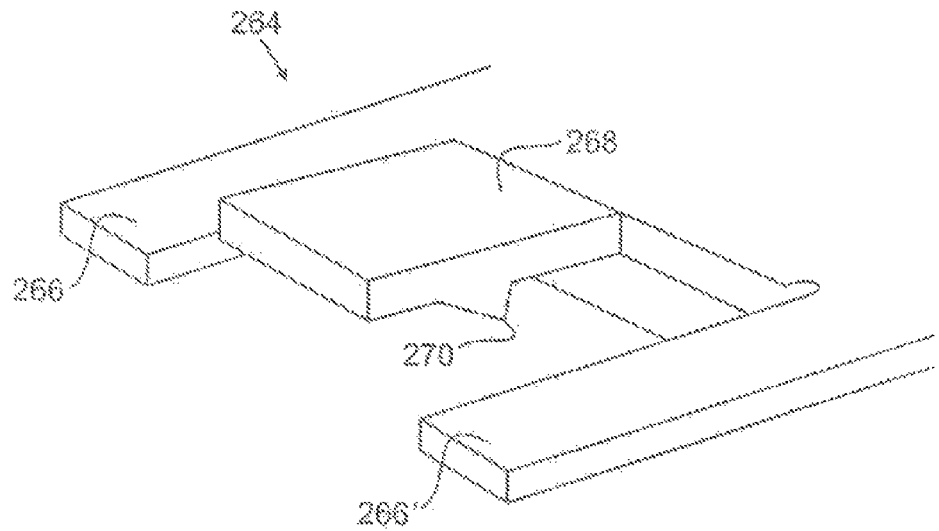
FIGS. 12(A) and 12(B) are perspective and side views, respectively, of a fourth embodiment of an attachment mechanism for attaching a device to a towel, e.g., here implemented as a flexible tab assembly.
Figure 12B:
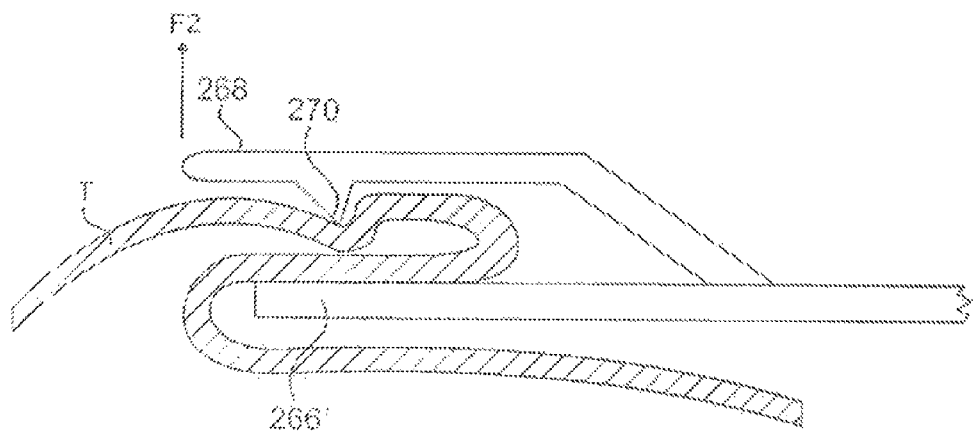

FIGS. 12(A) and 12(B) are perspective and side views, respectively, of a fourth embodiment of an attachment mechanism for attaching a device 110 to a towel, e.g., here implemented as a flexible tab assembly 264. While the device 110 is not shown in the figure, the same may be mounted on, coupled to, or formed integrally with the attachment mechanism. The flexible tab assembly 264 includes at least two tines 266 and 266' as well as a flexible tab 268. A burr 270 may be formed on the flexible tab 268 to allow an enhanced gripping effect on a towel portion T. As shown in FIG. 12(B), a towel portion T may be gathered and forced between the tines 266 and 266' and under the flexible tab 268. In this way, a towel may be secured in the flexible tab assembly 264, and thus the guidewire-loading device may be secured to a towel T. To release the towel, a force in the direction F2 may be exerted on the flexible tab 268.

Figure 13A:
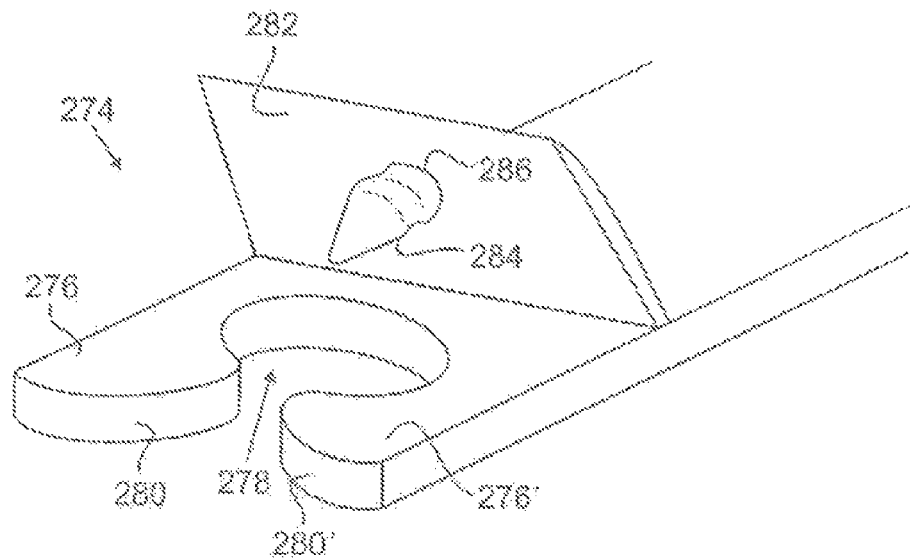
FIGS. 13(A) and 13(B) are perspective and side views, respectively, of a fifth embodiment of an attachment mechanism for attaching a device to a towel, e.g., here implemented as a hinged cover with a snap-button assembly.
Figure 13B:
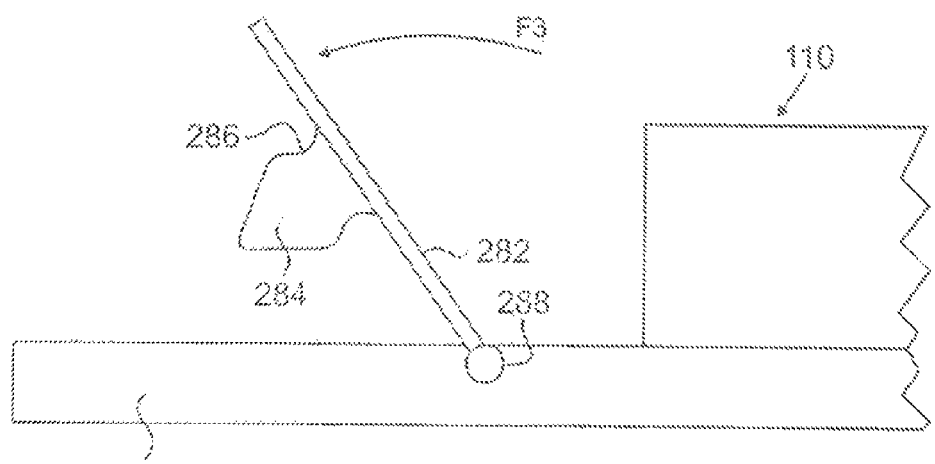

FIGS. 13(A) and 13(B) are perspective and side views, respectively, of a fifth embodiment of an attachment mechanism for attaching a device 110 to a towel, e.g., here implemented as a hinged cover with a snap-button assembly 274. In particular, two opposing segments 276 and 276' define a hole 278 into which a towel (not shown) may be drawn. The hole 278 is shown as substantially circular, but the shape is not critical. The segments 276 and 276' may include respective tapered surfaces 280 and 280' to ease introduction of a towel into the hole 278. A hinged cover 282 is shown, which is attached to the segments 276 and 276' by a hinge 288. A neck 286 extends from the cover 282, and a snap button 284 is attached to the neck 286.

When a towel portion has been pulled through the hole 278, the cover 282 may be closed in the direction indicated by arrow F3. This action secures the towel in the hole 278 and thus secures the guidewire-loading device to the towel. In one implementation, as shown, the snap button 284 has a bulbous shape; this shape assists in the securing of the snap button within the hole. However, other shapes may also be employed. For removal, the user may pull up on the cover 282 to pull the snap button 284 out of engagement with the hole 278.

Figure 14A:
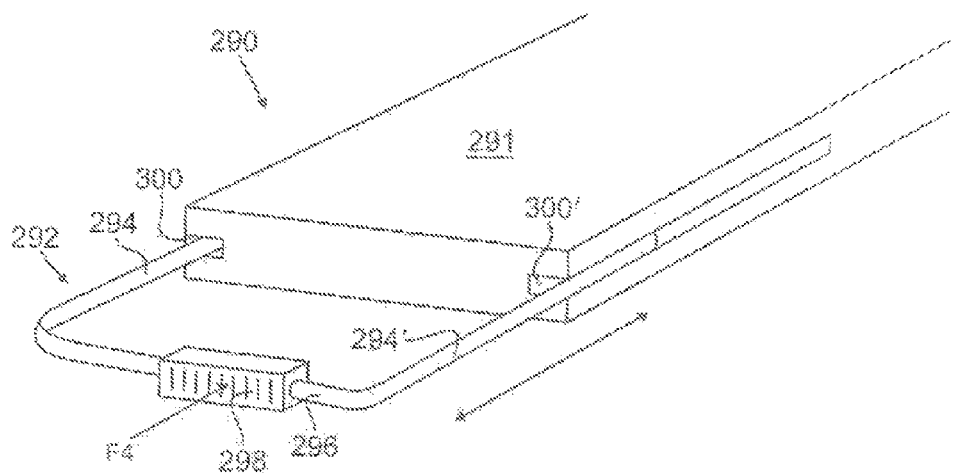
FIGS. 14(A) and 14(B) are perspective and side views, respectively, of a sixth embodiment of an attachment mechanism for attaching a device to a towel, e.g., here implemented as a sliding wire capture lock.
Figure 14B:
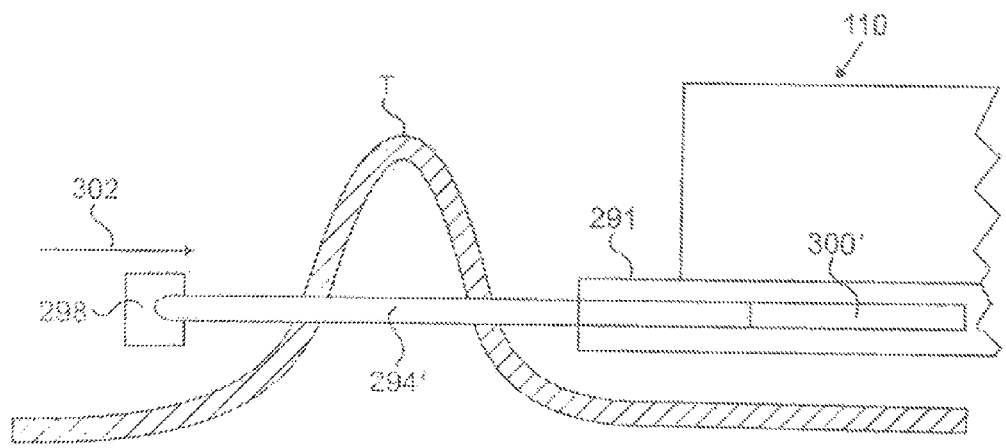

FIGS. 14(A) and 14(B) are perspective and side views, respectively, of a sixth embodiment of an attachment mechanism for attaching a device to a towel, e.g., here implemented as a sliding wire capture lock 290. As above, the same may be coupled to or formed integrally with a device 110. The sliding wire capture lock 290 includes a housing 91 in which are formed two slots 300 and 300'. A sliding wire 292 includes two longitudinal segments 294 and 294' which slide in the respective slots 300 and 300'. A cross segment 296 connects segments 294 and 294'. A tab 298 may be formed on the cross segment 296, to allow ease of pushing during installation and ease of pulling during removal. Ribbing, teeth, or other contouring may be employed on one or both sides of the tab 298 (as well as on a portion of the housing 291 facing the tab) to enhance the ability of a user to grip the tab 298 as well as to enhance gripping of a towel portion T. The tab 298 may extend along the any portion of the cross segment 296, include spanning the entire segment.

In use, a towel portion T is placed in the hole formed by segments 294, 294', 296, and the housing 291. The sliding wire 292 is then pushed toward the housing 291 in the direction indicated by arrow 302 (force F4). The towel T is thus captured, and the device 110 is thus secured to the towel T. For removal, the sliding wire 292 is pulled out in a direction opposite that of installation, and the towel T removed.

Figure 15A:
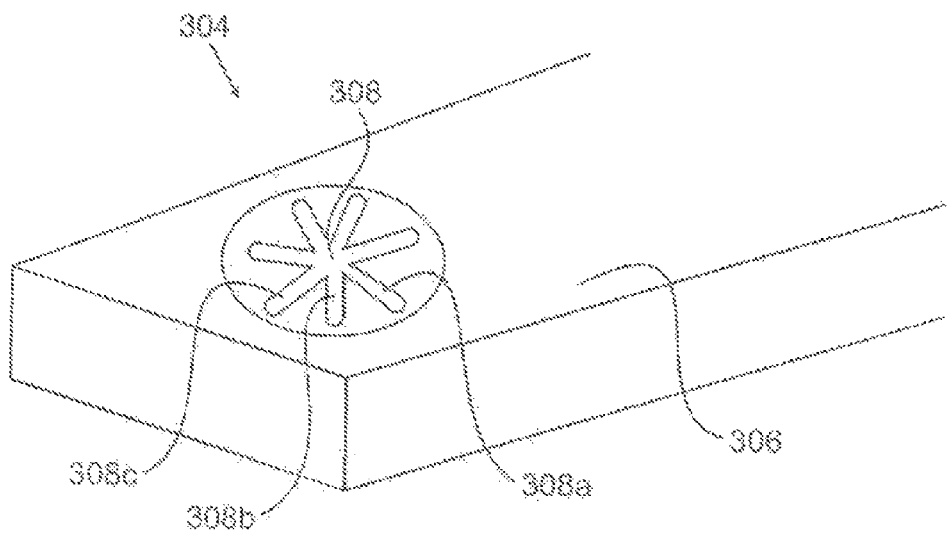
FIGS. 15(A) and 15(B) are perspective and side views, respectively, of a seventh embodiment of an attachment mechanism for attaching a device to a towel, e.g., here implemented as a gripping ring with flexible fingers.
Figure 15B:
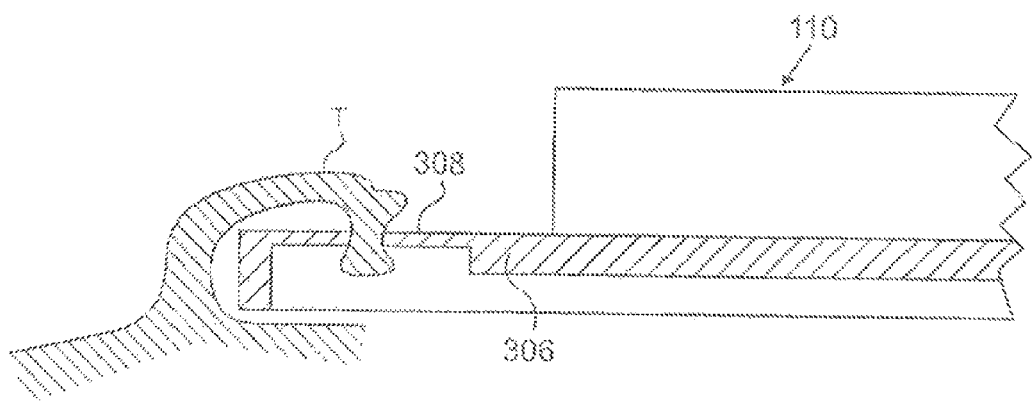

FIGS. 15(A) and 15(B) are perspective and side views, respectively, of a seventh embodiment of an attachment mechanism for attaching a device 110 to a towel, e.g., here implemented as a gripping ring assembly 304 with flexible fingers. This assembly 304 includes a housing 306 coupled to (or as above, integral with) the device 110 (shown in FIG. 15(B)). A gripping ring 308 is formed in the housing, and the same includes a number of flexible fingers 308a, 308b, and so on. The gripping ring 308 and flexible fingers 308i may be formed of, e.g., various plastic or rubber materials in order to allow sufficient flexibility to receive a portion of a towel T, secure the same against removal during normal use, and allow the towel to be removed following use. In use, as shown in FIG. 15(B), a portion of a towel T may be inserted into the gripping ring. The stiffness of the fingers 308i prevents removal of the towel until the procedure is completed, at which time the towel may be removed.

Figure 16A:
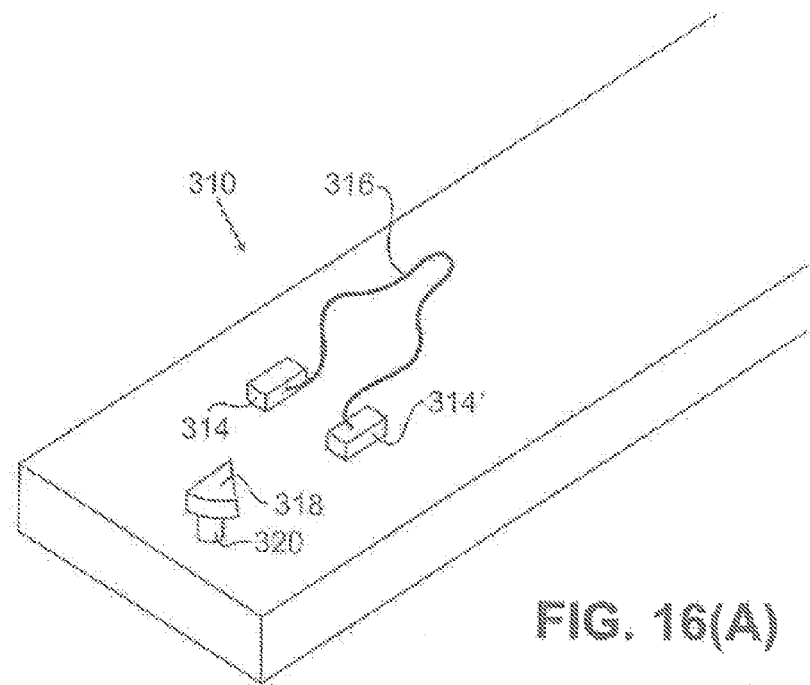
FIGS. 16(A) and 16(B) are perspective and side views, respectively, of a eighth embodiment of an attachment mechanism for attaching a device to a towel, e.g., here implemented as a capture wire with engagement button assembly.
Figure 16B:
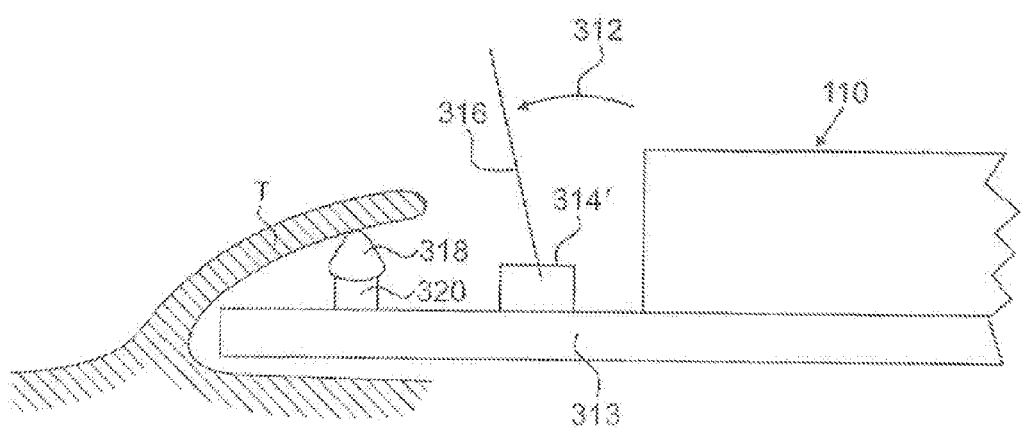

FIGS. 16(A) and 16(B) are perspective and side views, respectively, of an eighth embodiment of an attachment mechanism for attaching a device 110 to a towel, e.g., here implemented as a capture wire with engagement button assembly 110. The assembly 110 includes two supports 314 and 314' to which is mounted a capture wire 316. The supports 314 and 314' are mounted on a housing 313. Also mounted on the housing 113 is an engagement button 318 via a neck 320.

In use, a towel T is placed over the engagement button 318, and the capture wire 316 is then moved in an angular direction 312 and placed over the top of the towel T and the engagement button 318. The shape of the capture wire 316 and that of engagement button 318 may cooperate to secure the towel in position, or alternatively the securing may be accomplished only by way of friction fit with no particular shapes involved. To remove, the capture wire 316 is pulled away from the top of the engagement button 318, and the towel removed.

Suitable materials for use in major components of the attachment mechanisms are described above, as well as the device for catheter and guidewire management, include blow- or injection-molded plastics, or the like. The device for catheter and guidewire management may be single-use disposable or reusable.

The device may also be employed in a method for catheter and/or guidewire management. For example, in one exemplary method, the device for catheter and guidewire management may be employed to treat patients with "bifurcation lesions", i.e. the treatment of two vessels or branches simultaneously. Another application is a method of deploying rapid exchange catheters. When a rapid exchange catheter is first loaded on to a guidewire, the guidewire exits at the exit port, which is located about 22 cm from the catheter tip. An assistant holds the wire in place as the operator advances the catheter over the wire through the Y-adaptor and into the guide catheter towards the heart. Once the catheter has been advanced about 22 cm through the guide catheter, the portion of the guidewire external of the rapid exchange catheter is now confined by the guide catheter in such a way that the guidewire lies next to the catheter. The operator can now hold the wire with one hand while advancing the catheter with the other hand. In other words, for the first 22 cm, the assistant has to stop what they are doing and hold the wire in place for the operator. In a method employing a device for catheter or guidewire management, the device may be placed about 25 or 30 cm from the Y-adaptor. The rapid exchange catheter may be installed over the wire until the wire is emerging from the side of the catheter at the exit port and the catheter is about to enter the Y adaptor. The emerging portion of the guidewire may then be retained by any of the slits or grooves described, leaving the assistant free to perform other tasks. That is, the guidewire will then be held tightly by the slit so the catheter can be advanced through the Y-adaptor into the patient without the guidewire moving inside the artery. In some cases, two devices may then be used, one to retain the guidewire, and one to keep the multiple wires and catheters organized. Methods for installing other catheters will also be apparent given this disclosure.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

The invention claimed is:

1. A device for managing associated pairs of flexible elongated members on a surgical field, the device comprising:
   a housing including at least three vertical supports each extending from a respective support base end to a respective support top end, the vertical supports defining at least two retaining member housings having open tops formed by spacing between support top ends of sequential vertical supports;
   means for holding the housing in a selected position and orientation on the surgical field; and
   at least one pair of retaining members disposed in the at least two retaining member housings, each retaining member configured to be disposed in a respective retaining member housing,
   each of the pair of retaining members having a member base end surrounded by neighboring respective support base ends, a member top end adjacent respective support top ends, and a v-shaped slot originating at the member top end and extending in a direction of the member base end, each v-shaped slot configured to receive at least one flexible elongated member in a selected position.

2. The device recited in claim 1, wherein at least one of the pair of retaining member includes another v-shaped slot originating at the member top end, wherein the two v-shaped slots of the at least one retaining member extend side-by-side in the direction of the member base end, and wherein a taper of a first of the two v-shaped slots is different from a taper of a second of the two v-shaped slots.

3. The device recited in claim 2, wherein the taper of the first v-shaped slot is sized to receive a catheter, and wherein the taper of the second v-shaped slot is sized smaller to receive a guidewire.

4. The device recited in claim 1, wherein the means for holding the housing in the selected position and orientation on the surgical field includes an attachment mechanism coupled to the housing for securing the housing to a fabric.

5. The device recited in claim 4, wherein the attachment mechanism is selected from the group consisting of: towel clamps with springs or clips, flexible fork assemblies, flexible tabs, hinged tabs, wire capture systems, gripping rings with flexible fingers, wire-and-plug capture systems, at least one protuberance, and opposing finger towel capture systems.

6. The device recited in claim 5, wherein the attachment mechanism is an opposing finger towel capture system, and wherein the opposing finger towel capture system is disposed on at least two substantially opposite sides of the housing.

7. The device recited in claim 1, further comprising protuberances disposed on a bottom surface of the housing.

8. The device recited in claim 1, wherein a bottom surface of the housing opposite a top surface from which the at least three vertical supports extend is curved.

9. The device recited in claim 1, wherein a top surface of the housing from which the at least three vertical supports extend is curved.

10. The device recited in claim 1, wherein each retaining member includes another v-shaped slot formed therein, wherein the two v-shaped slots of each retaining member extend side-by-side, and wherein a shape of a first of the two v-shaped slots is the same as a shape of a second of the two v-shaped slots.

11. The device recited in claim 1, wherein each retaining member has a durometer of between 30-80 Shore hardness, inclusive, configured such that a user determines, by how far the flexible elongated member is inserted into the v-shaped slot, whether the flexible elongated member is held against transverse movement only or against both transverse and longitudinal movements.

12. The device recited in claim 1, wherein a portion of each support top end and a portion of each member top end are coplanar.

13. The device recited in claim 1, wherein each v-shaped slot extends into a ribbed slot defined by a first finger, including a first rib and a first indentation, and a second finger, including a second rib and a second indentation, the first rib is sized and shaped to fit into the second indentation and the second rib is sized and shaped to fit into the first indentation.

14. A device for managing a flexible elongated member on a surgical field, the device comprising:
 a housing including a plurality of vertical supports, the vertical supports each extending from a respective support base end to a respective support top end and defining one or more retaining member housings therebetween,
 the one or more retaining member housings having a closed base, formed by a support base end of a first vertical support, a support base end of an adjacent second vertical support and a connection member that connects the two support base ends, and an open top, formed by a spacing between a support top end of the first vertical support and a support top end of the second vertical support;
 at least one retaining member disposed in the one or more retaining member housings by way of the open top and including a substantially v-shaped slot originating at the open top to retain at least one flexible elongated member in a selected position,
 the retaining member having a durometer of between 30-80 Shore hardness, configured such that a user may select, by how far the flexible elongated member is inserted into the substantially v-shaped slot, whether the flexible elongated member is held against transverse movement only or against both transverse and longitudinal movements; and
 an attachment mechanism for holding the housing onto the surgical field, the attachment mechanism including an opposing finger towel capture system.

15. The device recited in claim 14, wherein the substantially v-shaped slot includes at least two surfaces forming an angle of between 2 and 10 degrees, inclusive.

16. The device recited in claim 14, wherein the substantially v-shaped slot includes at least two surfaces forming an angle of between 1 and 2 degrees, inclusive.

17. The device recited in claim 14, wherein the at least one retaining member includes another substantially v-shaped slot originating at the open top, wherein the two substantially v-shaped slots of the at least one retaining member extend side-by-side in the direction opposite the open top, and wherein a taper of a first of the two substantially v-shaped slots is different from a taper of a second of the two v-shaped slots.

18. The device recited in claim 14, wherein a bottom surface of the housing opposite a top surface from which the plurality of vertical supports extend is curved.

19. The device recited in claim 14, wherein the support top ends of the plurality of vertical supports include a triangular profile.

20. The device recited in claim 14, wherein the substantially v-shaped slot extends into a ribbed slot defined by a first finger, including a first rib and a first indentation, and a second finger, including a second rib and a second indentation, the first rib is sized and shaped to fit into the second indentation and the second rib is sized and shaped to fit into the first indentation.

21. A device for managing associated pairs of flexible elongated members on a surgical field, the device comprising:
 a housing;
 at least one pair of retaining members disposed in the housing, the retaining members collectively including a first substantially v-shaped slot to accommodate a first flexible elongated member and a second substantially v-shaped slot to accommodate a second flexible elongated member,
 the first and second substantially v-shaped slots each extend into respective ribbed slots, the ribbed slots each defined by a first finger, including a first rib and a first indentation, and a second finger, including a second rib and a second indentation, the first rib is sized and shaped to fit into the second indentation and the second rib is sized and shaped to fit into the first indentation; and
 an attachment mechanism for holding the housing onto the surgical field, the attachment mechanism including an opposing finger towel capture system.

22. The device recited in claim 21, wherein the first substantially v-shaped slot is configured for a catheter, and wherein the second substantially v-shaped slot is configured for a guidewire.

* * * * *